United States Patent
M'Koma

(10) Patent No.: US 12,174,200 B2
(45) Date of Patent: *Dec. 24, 2024

(54) TARGETED HD5 ANTIBODY AND ASSAY METHODS FOR DIAGNOSING AND TREATING INFLAMMATORY BOWEL DISEASE

(71) Applicant: Meharry Medical College, Nashville, TN (US)

(72) Inventor: Amosy E. M'Koma, Nashville, TN (US)

(73) Assignee: Meharry Medical College, Nashville, TN (US)

( * ) Notice: Subject to any disclaimer, the term of this patent is extended or adjusted under 35 U.S.C. 154(b) by 896 days.

This patent is subject to a terminal disclaimer.

(21) Appl. No.: 16/622,259

(22) PCT Filed: Jun. 20, 2018

(86) PCT No.: PCT/US2018/038582
§ 371 (c)(1),
(2) Date: Dec. 12, 2019

(87) PCT Pub. No.: WO2018/237064
PCT Pub. Date: Dec. 27, 2018

(65) Prior Publication Data
US 2021/0278417 A1  Sep. 9, 2021

Related U.S. Application Data

(60) Provisional application No. 62/522,652, filed on Jun. 20, 2017.

(51) Int. Cl.
| | | |
|---|---|---|
| A61K 31/573 | (2006.01) | |
| C12Q 1/6883 | (2018.01) | |
| G01N 33/50 | (2006.01) | |
| G01N 33/68 | (2006.01) | |

(52) U.S. Cl.
CPC ....... *G01N 33/6893* (2013.01); *C12Q 1/6883* (2013.01); *C12Q 2600/106* (2013.01); *C12Q 2600/158* (2013.01); *G01N 2333/4721* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 11,427,852 B2 * | 8/2022 | M'Koma | ............. C12Q 1/6876 |
| 2009/0155788 A1 | 6/2009 | Abbas et al. | |
| 2010/0004213 A1 * | 1/2010 | Abbas | ....................... A61P 1/00 |
| | | | 435/6.16 |
| 2014/0179620 A1 * | 6/2014 | Abbas | ................... A61K 31/56 |
| | | | 435/7.1 |
| 2015/0253342 A1 | 9/2015 | Ataman-Onal et al. | |

FOREIGN PATENT DOCUMENTS

WO  WO-2006063133 A2 *  6/2006  ........... A61K 31/573

OTHER PUBLICATIONS

Arijs et al. Mucosal Gene Expression of Antimicrobial Peptides in Inflammatory Bowel Disease Before and After First Infliximab Treatment. PLoS ONE. 4(11): e7984: Published: Nov. 24, 2009 (Year: 2009).*
Noble et al. Regional variation in gene expression in the healthy colon is dysregulated in ulcerative colitis. Gut. 57: 1398-1405; Published: Jun. 3, 2008 (Year: 2008).*
Wehkamp et al. Reduced Paneth cell-defensins in ileal Crohn's disease. PNAS. 102(50): 18129-18134: Published: Dec. 13, 2005 (Year: 2005).*
Emd Millipore, Anti-Alpha Defensin-5 (HD5) Antibody, clone 8C8, 2020, available at: http://www.emdmillipore.com/US/en/product/Anti-Alpha-Defensin-5-HD5-Antibody-clone-8C8,MM_NF-MABF31.
Williams et al. Human alpha defensin 5 is a candidate biomarker to delineate inflammatory bowel disease., PloS One, 2017, p. e0179710, vol. 12, No. 8.

* cited by examiner

*Primary Examiner* — Juliet C Switzer
*Assistant Examiner* — Katherine Ann Holtzman
(74) *Attorney, Agent, or Firm* — Bradley Arant Boult Cummings LLP; Phil Walker; Jessica L. Zurlo

(57) ABSTRACT

A targeted DEFA5 antibody is disclosed herein. The targeted DEFA5 antibody has a high degree of specificity with DEFA5 protein, particularly with peptide sequences of the P, B, and/or M binding sites of the DEFA5 protein. The targeted DEFA5 antibody may be incorporated into an assay for diagnosing and treating ulcerative colitis and Crohns disease in a subject suffering from inflammatory bowel disease. The assay may be provided in a kit. The targeted DEFA5 antibody may be used in a method for measuring the level of DEFA5 or DEFA5 expression in a sample collected from a subject, and determining, based on the level of DEFA5 or DEFA5 expression, whether the subject is suffering from ulcerative colitis or Crohns disease. A treatment may be based on the determination of whether the subject has ulcerative colitis or Crohns disease.

9 Claims, 11 Drawing Sheets
Specification includes a Sequence Listing.

A

```
       HD5 (SEQ ID NO: 1) versus HD1 (SEQ ID NO: 2)
HD5  1  MRTIAILAAILLVALQAQAESLQERADE-ATTQKQSGEDNQDLAISFAGNGLSALRTSGS  59
        MRT+AILAAILLVALQAQAE LQ RADE A   +Q   D  ++ +S A +   A  + GS
HD1  1  MRTLAILAAILLVALQAQAEPLQARADEVAAAPEQIAADIPEVVVSLAWDESLAPKHPGS  60

HD5 60  QARATCYCRTGRCATRESLSGVCEISGRLYRLCC  93
         +   CYCR  C   E   G C    GRL+  CC
HD1 61  RKNMACYCRIPACIAGERRYGTCIYQGRLWAFCC  94

HD5 (SEQ ID NO: 1) versus HD6 (SEQ ID NO: 6)
HD5  1  MRTIAILAAILLVALQAQAESLQERAD-------EATTQKQSGEDNQDLAISFAGNGLSA  53
        MRT+ IL A+LLVALQA+AE LQ   D       EA  Q+QG  ++QD A+SFA +  S+
HD6  1  MRTLTILTAVLLVALQAKAEPLQAEDDPLQAKAYEADAQEQRGANDQDFAVSFAEDASSS  60

HD  54  LRTSGSQARATCYCRTGRCATRESLSGVCEISGRLYRLCC  93
        LR GS    TC+CR  C + E   G C + G +R CC
HD6 61  LRALGSTRAFTCHCRRS-CYSTEYSYGTCTVMGINHRFCC  99
```

B

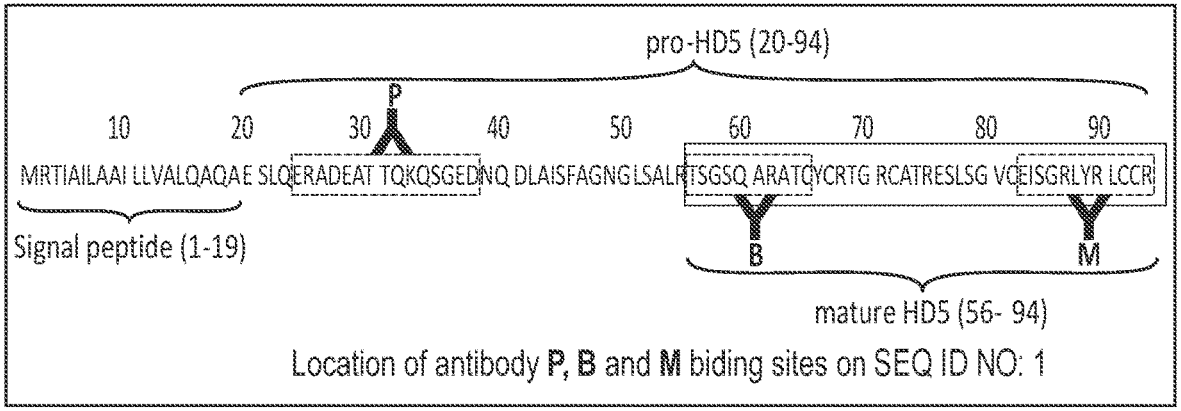

Location of antibody P, B and M binding sites on SEQ ID NO: 1

C

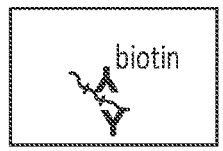 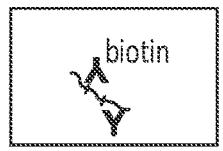 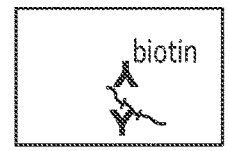

ELISA Formats

*FIG. 2*

TARGETED HD5 ANTIBODY AND ASSAY METHODS FOR DIAGNOSING AND TREATING INFLAMMATORY BOWEL DISEASE

CROSS-REFERENCE TO RELATED APPLICATIONS

This application cites and claims priority of U.S. Patent Application No. 62/522,652, filed Jun. 20, 2017.

STATEMENT REGARDING FEDERALLY SPONSORED RESEARCH OR DEVELOPMENT

This invention was made with government support under grant numbers R21DK095186; U54CA091408-09S1; U54CA091408-09S2; U54RR026140; U54MD007593; UL1RR024975; UL1TR000445; G12MD007586; U54CA163069; R24 DA036420; and S10RR0254970 awarded by the National Institute of Health. The government has certain rights in the invention.

In this context "government" refers to the government of the United States of America.

INCORPORATION BY REFERENCE OF SEQUENCE LISTING

A Sequence Listing is provided herewith as a text file, "MKonaAbSeq_ST25.txt," created on Jun. 20, 2017 and having a size of 5 KB. The contents of the text file are incorporated by reference herein in their entirety.

BACKGROUND OF THE DISCLOSURE

Inflammatory bowel disease (IBD) is the chronic inflammation of all, or part of, the digestive tract. Common causes of IBD include ulcerative colitis ("UC") and Crohn's disease, also known as Crohn's colitis ("CD" or "CC"). Ulcerative colitis causes chronic inflammation and ulcers in the innermost lining of the large intestine, i.e. the colon, and rectum. Crohn's disease causes chronic inflammation of the lining of the digestive tract, where inflammation goes beyond the lining and into affected tissue. Crohn's disease can affect the small intestine, large intestine, or both.

UC and CD affect an estimated 1.6 million people in the US alone with associated annual health care costs of over $6.3 billion. While UC and CD are both types of IBDs, differences between patients having UC or CD have major implications. Currently, clinicians use inexact combined classifications for patients having IBD, which include clinical, endoscopy, radiological, and histopathology in an effort to diagnose CD and UC. Nonetheless, differentiating patients having UC or CD among patients suffering from IBD remains challenging, so much so that cases of patients having IBD that are difficult to classify as UC or CD are classified as having indeterminate colitis ("IC"). A significant subgroup of IBD patients are misdiagnosed or have a correct diagnosis delayed despite use of a state-of-the-art classification system applying clinical, endoscopic, radiologic, and histologic tools. Indeed, it is estimated that 30% of patients suffering from IBD cannot currently be accurately diagnosed as CD or UC.

In addition, 15% of colonic IDB cases that undergo ileal pouch anal anastomosis surgery, as they are diagnosed with UC, will subsequently have their original diagnosis changed to CD based on their postoperative follow-up visits, clinical and histopathology changes, and development of de novo CD in the ileal pouch. Ileal pouch anal anastomosis, a treatment normally suitable for UC but not CD, restores gastrointestinal continuity after surgical removal of the colon and rectum, and involves the creation of a pouch of small intestine to recreate the removed rectum.

Implications of distinguishing cases of UC and CD include choice of medical treatment, timing of surgery, prognosis, whether to offer the patient an ileal pouch anal anastomosis, and lifestyle expectations. For these reasons, there is a need for improving the diagnosis, and subsequent treatment, of subjects having IBD.

SUMMARY

It has been discovered that the DEFA5 protein (e.g., HD5), and the expression of the DEFA5 gene, may serve as a biomarker for determining whether a patient suffering from IBD has UC or CD. In particular, an anti-DEFA5 antibody has been identified and discovered that has high specificity for binding with DEFA5 while not binding with other defensin proteins that is highly advantageous for identifying DEFA5 as a biomarker in subjects.

In a first aspect, a method of measuring DEFA5 protein in a patient suffering from or at risk of inflammatory bowel disease (IBD) is disclosed. The method includes measuring the level of DEFA5 or DEFA5 expression in a sample from the subject using an anti-DEFA5 antibody.

In a second aspect, a method of treating a patient suffering from or at risk of IBD is disclosed. The method includes measuring the level of DEFA5 or DEFA5 expression in a sample from the subject using an anti-DEFA5 antibody and performing an intervention on the patient to treat Crohn's disease. The method may further comprise comparing the expression of DEFA5 or the concentration of DEFA5 in the sample to a benchmark value that is typical of a subject not suffering from Crohn's disease; and diagnosing Crohn's disease if the expression of DEFA5 or the concentration of DEFA5 in the sample significantly exceeds the benchmark value.

In a third aspect, a method diagnosing a subject suffering from or at risk of CD is provided, comprising measuring the level of DEFA5 or DEFA5 expression in a sample from the subject using an anti-DEFA5 antibody; comparing the expression of DEFA5 or the concentration of DEFA5 in the sample to a benchmark value that is typical of a subject not suffering from Crohn's disease; and diagnosing Crohn's disease if the expression of DEFA5 or the concentration of DEFA5 in the sample significantly exceeds the benchmark value.

In a fourth aspect, a method for treating a patient suffering from or at risk of UC is disclosed. The method comprises performing the method of measuring DEFA5 in the patient according to the first aspect; and performing an intervention on the patient to treat ulcerative colitis. The method may further comprise comparing the expression of DEFA5 or the concentration of DEFA5 in the sample to a benchmark value that is typical of a subject not suffering from Crohn's disease; and diagnosing ulcerative colitis if the expression of DEFA5 or the concentration of DEFA5 in the sample does not significantly exceed the benchmark value.

In a fifth aspect, a kit for measuring DEFA5 in a sample is provided. The kit comprises an assay comprising an anti-DEFA5 antibody; and a sample container configured to contain a sample selected from: a stool sample, a blood sample, a bowel tissue sample, and a serum sample. The kit may be for the diagnosis, and subsequent treatment of, inflammatory bowel disease. The kit comprises any of the anti-DEFA5 antibodies disclosed herein as part of immunoassay. The antibodies may be tagged, conjugated, truncated, or otherwise modified to function in the assay as is known in the art. The kit may further comprise one or more of a sample container and a sampling tool. The container and sampling tool may be configured to collect and store various types of samples including a stool sample, a blood sample, a serum sample, a rectal lavage sample, and a biopsy sample. The sampling tool may be any of a biopsy instrument, a rectal lavage kit, a swab, a blood sampler, and a vacutainer.

In a sixth aspect, a method of diagnosing and treating Crohn's disease in a subject suffering from inflammatory bowel disease is provided. The method includes obtaining a sample from the patient; measuring the concentration of human DEFA5 in the sample using an anti-DEFA5 antibody having a higher affinity for human DEFA5 than for either of human DEFA1 or human DEFA6; comparing the concentration of DEFA5 in the sample to a benchmark value that is typical of a subject not suffering from Crohn's disease; diagnosing Crohn's disease if the concentration of DEFA5 in the sample significantly exceeds the benchmark value; and treating the subject for Crohn's disease by way of a non-surgical intervention.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present concepts in a simplified form as a prelude to the more detailed description that is presented later.

BRIEF DESCRIPTION OF THE DRAWINGS

FIG. 2A illustrates an alignment of the primary sequence of DEFA5 with that of HD1 and HD6.

FIG. 2B is a schematic showing DEFA5 antibody epitopes to distinguish pro-DEFA5 from mature protein in sera of IBD patients.

FIG. 2C is a model of sandwich ELISA to be used to detect pro-DEFA5 and mature DEFA5 in sera of IBD patients.

DETAILED DESCRIPTION

Figure 1:
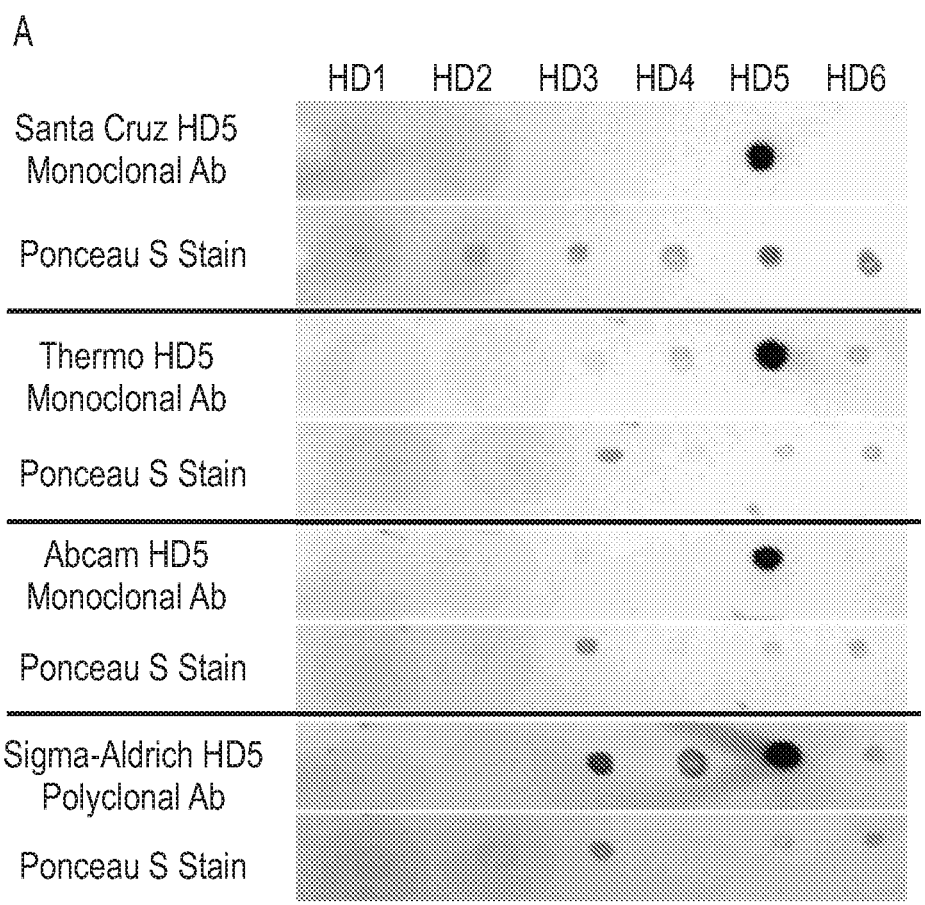
FIG. 1 is a dot staining of HD1 to HD6 specificity of commercially available DEFA5 antibodies.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense, unless expressly so defined herein. Well-known functions or constructions may not be described in detail for brevity or clarity.

The terminology used herein is for the purpose of describing particular embodiments only and is not intended to be limiting. As used herein, the singular forms "a", "an," and "the" are intended to include the plural forms as well, unless the context clearly indicates otherwise.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20%, preferably within 10%, and more preferably within 5% of a given value or range of values. For biological systems, the term "about" refers to an acceptable standard deviation of error, preferably not more than 2-fold of a given value. Numerical quantities in this detailed description are approximate unless stated otherwise, meaning that the term "about" or "approximately" can be inferred when not expressly stated.

The terms "individual," "subject," or "patient" as used herein refer to any animal, including mammals, such as mice, rats, other rodents, rabbits, dogs, cats, swine, cattle, sheep, horses, primates, and humans. The terms may specify male or female or both, or exclude male or female.

The terms "treatment", "treat", and "treating", as used herein, refer to a course of action (such as administering a compound or pharmaceutical composition) initiated after the onset of a clinical manifestation of a disease state or condition so as to eliminate or reduce such clinical manifestation of the disease state or condition.

Such treating need not be absolute to be useful.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

DEFA5 is a small, microbicidal innate immune system protein belonging to the alpha defensin family of mammalian defensin peptides. DEFA5 is expressed in various tissues and particularly on mucosal surfaces. DEFA5 is encoded by the gene DEFA5. DEFA5 is involved in host defense mechanisms and is highly expressed in secretory granules of Paneth cells of the small intestine (ileum). Like most secreted proteins, DEFA5 is synthesized as prepro-DEFA5 (1-94) that undergoes proteolytic processing first, to the inactive pro-DEFA5s (20-94), DEFA5 (23-94), and DEFA5 (29-94). DEFA5 (23-94) and DEFA5 (29-94) are found within tissues, while DEFA5 (20-94) is the predominant intracellular form. The pro-DEFA5s are then processed to two active or mature forms. DEFA5 (56-94) and DEFA5 (63-94) with DEFA5 (63-94) being the most abundant form. These mature forms of DEFA5 are cysteine-rich host defense peptides which exert broad-spectrum antimicrobial activity and contribute to innate immunity in the human gut. As used herein, DEFA5 may refer to exclusively mature forms of DEFA5.

Methods of using an anti-DEFA5 antibody are described herein, whereby the anti-DEFA5 antibody is used in the detection, measurement, and/or treatment of patients having IBD. The anti-DEFA5 antibody forms a complex with DEFA5 that is relatively stable under physiologic conditions. Specific binding can be characterized by an equilibrium dissociation constant of at least about $1 \times 10^{-6}$ M or less (e.g., a smaller KD denotes a tighter binding). Methods for determining whether two molecules specifically bind are well known in the art and include, for example, equilibrium dialysis, surface plasmon resonance, and the like. An anti-DEFA5 antibody may, however, exhibit cross-reactivity to other antigens such as DEFA5 molecules from other species. Moreover, multi-specific antibodies (e.g., bispecifics) that bind to DEFA5 and one or more additional antigens are nonetheless considered anti-DEFA5 antibodies, as used herein. As used herein, an "anti-DEFA5 antibody" is an antibody that forms a stable complex with DEFA5 under expected binding conditions (e.g., physiological conditions).

The anti-DEFA5 antibody may bind to DEFA5 at various levels of affinity. One embodiment of the anti-DEFA5 antibody is a high affinity anti-DEFA5 antibody. The term "high affinity" antibody refers to an antibody having a binding affinity to DEFA5 of at least $10^{-10}$ M; preferably $10^{-11}$ M; even more preferably $10^{-12}$ M, as measured by surface plasmon resonance, e.g., BIACORE™ or solution-affinity ELISA.

The anti-DEFA5 antibody may bind to DEFA5 with high affinity ("high-affinity anti-DEFA5 antibody"). As used herein, a "high affinity anti-DEFA5 antibody" is an antibody that has a high binding affinity. "High binding affinity" refers to a high strength with which the epitope binds to an individual paratope (antigen-binding cite). Antibodies that have a high binding affinity bind more quickly to the antigen, permit greater sensitivity in assays, and better maintain a bond with the paratope when compared to an antibody having a lower affinity. The anti-DEFA5 antibody described herein may have a binding affinity to DEFA5 of at least as low as $10^{-7}$, $10^{-8}$, $10^{-9}$, $10^{-10}$, $10^{-11}$, or $10^{-12}$ $K_Ds$ (M), or any range or subvalue thereof, The term "$K_D$" refers to the equilibrium dissociation constant of a particular antibody-antigen interaction, or the equilibrium dissociation constant of an antibody, antibody binding fragment, or molecular interaction. The equilibrium dissociation may be calculated by obtaining the dissociation rate constant (koff value) of a particular antibody-antigen interaction, with the association rate constant of a particular antibody-antigen interaction. A lower KD value indicates a higher binding affinity.

The anti-DEFA5 antibody described herein may also have a high specificity to DEFA5. A "specificity" refers to the ability to bind to a particular antigen, but not other antigens. Some embodiments of the anti-DEFA5 antibody display an affinity for DEFA5 that exceeds a displayed affinity to one or more related proteins; such related proteins may include one or more of DEFA1, DEFA2, DEFA3, DEFA4, and DEFA6. These are related neutrophil defensins found in multiple species. The canonical human neutrophil defensin 1 protein (DEFA1) is described at UniProt Accession No. P59665, the sequence of which is provided herein as SEQ ID NO: 2. The canonical human neutrophil defensin 2 protein (DEFA2) is described at UniProt Accession No. P59665, the sequence of which is provided herein as SEQ ID NO: 3. The canonical human neutrophil defensin 3 protein (DEFA3) is described at UniProt Accession No. P59666, the sequence of which is provided herein as SEQ ID NO: 4. The canonical human neutrophil defensin 4 protein (DEFA4) is described at UniProt Accession No. P12838, the sequence of which is provided herein as SEQ ID NO: 5. The canonical human neutrophil defensin 6 protein (DEFA6) is described at UniProt Accession No. P12838, the sequence of which is provided herein as SEQ ID NO: 6. Further embodiments of the high specificity anti-DEFA5 antibody display a higher affinity to DEFA5 than to DEFA1, DEFA6, or both. In an embodiment, the anti-DEFA5 antibody has a high specificity to DEFA5 and does not bind, or substantially does not bind (i.e., has a low or no binding affinity), to HD1 and HD6. The anti-DEFA5 antibody may have a binding affinity to HD1 and/or HD6 of greater than about $10^{-10}$, $10^{-9}$, $10^{-8}$, $10^{-7}$, $10^{-6}$, $10^{-5}$, $10^{-4}$, $10^{-3}$, $10^{-2}$, $10^{-1}$ $K_Ds$ (M), or any range or subvalue thereof. The anti-DEFA5 antibody may have a $K_Ds$ (M) with one or both of DEFA1 and DEFA6 that is greater than one of the following values: $10^{-10}$, $10^{-9}$, $10^{-8}$, $10^{-7}$, $10^{-6}$, $10^{-5}$, $10^{-4}$, $10^{-3}$, $10^{-2}$, and $10^{-1}$. The anti-DEFA5 antibody may recognize an epitope binding region having at least 80%, 85%, 90%, 92%, 94%, 96%, or 98% sequence identity to positions 51-94 of SEQ ID NO: 1. The anti-DEFA5 antibody may recognize an epitope binding region having 100% sequence identity to positions 51-94 of SEQ ID NO: 1. Some embodiments of the anti-DEFA5 antibody do not recognize an epitope binding region having at least 80%, 85%, 90%, 92%, 94%, 96%, or 98% sequence identity to positions 1-49 of SEQ ID NO: 1. A specific embodiment of the anti-DEFA5 antibody does not recognize an epitope binding region having 100% sequence identity to positions 1-49 of SEQ ID NO: 1.

Examples of commercially available anti-DEFA5 antibodies include: Anti-alpha 5 Defensin antibody [EPR14309 (B)] from ABCAM, Cambridge, United Kingdom; Anti-alpha 5 Defensin antibody (ab167591) from ABCAM, Cambridge, United Kingdom; Anti-alpha 5 Defensin antibody [8C8] (Catalogue #ab90802) from ABCAM, Cambridge, United Kingdom; Defensin 5 Monoclonal Antibody (8C8) (Catalogue #MA1-46026) from THERMO FISHER SCIENTIFIC INC., Waltham, MA; Anti-Alpha Defensin-5 (DEFA5) Antibody, clone 8C8 (Catalogue #MABF31) from MILLIPORESIGMA, Burlington, MA; Defensin 5 Antibody LS-C50934 (Catalogue #LS-C50934-100) from LSBIO, Seattle, WA; Defensin alpha 5 Antibody (8C8) (Catalogue #NB110-60002/NB110-60002SS) from NOVUS BIOLOGICALS, Littleton, CO; Defensin alpha 5 Antibody (8C8) (Catalogue #NBP1-84282) from NOVUS BIOLOGICALS, Littleton, CO; Defensin alpha 5 antibody (Catalogue #orb156565) from BIORBYT, Cambridge, United Kingdom; Defensin alpha 5 Antibody (Catalogue #bs-4313R) from BIOSS INC., Woburn, MA; Defensin alpha 5 antibody [N1C3] (Catalogue #GTX116079) from GENETEX, INC., Irvine, CA; Anti-DEFA5 Antibody (HPA015775) from ATLAS ANTIBODIES, Bromma, Sweden; DEFA5 antibody (catalogue number 972207.111 or CSL 1450400) from R&D SYSTEMS, Minneapolis, MN; and α-defensin 5 antibody (catalogue #53997) from SANTA CRUZ BIOTECHNOLOGY, INC., Dallas, TX, among many others.

In one embodiment, the anti-DEFA5 antibody is α-defensin 5 antibody (catalogue #53997) from SANTA CRUZ BIOTECHNOLOGY, INC., Dallas, TX Surprisingly, it has been discovered that the α-defensin 5 antibody (catalogue #53997) is particularly advantageous for measuring the levels of DEFA5 and DEFA5 expression in a sample. In particular, the α-defensin 5 antibody (catalogue #53997) displays a high affinity and high specificity for DEFA5, including the high affinity and high specificity for HD5 and low to no affinity and specificity for other defensins, such as HD1-HD4 or HD6. The anti-DEFA5 antibody may be a kappa light chain polypeptide subunit. In some embodiments, the anti-DEFA5 antibody is a mammalian antibody, such as a human antibody or a canine antibody.

A method of diagnosing ulcerative colitis or Crohn's disease in a subject is disclosed. The subject may have IBD. The method includes measuring the level of α-defensin 5 ("DEFA5") or DEFA5 expression in a sample from the subject using a anti-DEFA5 antibody, and diagnosing the subject as suffering from Crohn's disease if the level or expression of DEFA5 is indicative of a subject having Crohn's disease; or diagnosing the subject as suffering from ulcerative colitis if the level or expression of DEFA5 is indicative of a subject having ulcerative colitis. The sample can be taken from any suitable source for measuring DEFA5 concentration, DEFA5 expression levels, such as tissue samples from the intestine, such as from the large intestine or rectum. In this disclosure the term "expression of DEFA5" should be interpreted to mean the expression of the DEFA5 gene; "levels of DEFA5" should be interpreted to mean the concentration of DEFA5 protein.

The sample may be taken from a subject who is suffering from or at risk of IBD. The subject may display one or more symptoms characteristic of IBD, such as severe diarrhea, abdominal pain, fatigue, and weight loss. In some embodiments of the method, the subject displays more than one of said symptoms. In further embodiments the subject displays two, three, or four of said symptoms.

It has been discovered that DEFA5 is differentially expressed in subjects having UC and CD. Used in this way, DEFA5 concentration and DEFA5 expression can be utilized and measured, using the targeted DEFA5 antibody, as a biomarker for distinguishing UC and CD in patients having IBD. As ileal pouch anal anastomosis is clinically much more successful in patients having UC than in patients suffering from CD, patients identified as having levels of DEFA5 indicative of UC, or not having CD, may be treated with ileal pouch anal anastomosis. Indeed, as DEFA5 is produced by Paneth cells only, one would not expect to find Paneth cells that secret DEFA5 in the colon. It has been discovered that Paneth cells (secreting DEFA5) are abundantly found in subjects having CC. On the other hand, patients identified as having levels of DEFA5 and DEFA5 expression indicative of CD may be treated with any suitable treatment for CD. In an embodiment, a diagnosing step, such as diagnosing a subject with UC or CD, is optional.

The anti-DEFA5 antibody may have a complementarity determining region (CDR) that is complementary to each of, or all of, the DEFA5 sequence of the P, B, and M binding sites of DEFA5, as shown in FIG. 2. As used herein, "complementary to" means that the CDR is capable of forming a stable complex with the target sequence (e.g., the P, B, or M binding sites) under expected binding conditions (e.g., physiological conditions).

In another embodiment, the antibody may be an antibody having a certain degree of identity to a polypeptide sequence complementary to the P, B, and M binding sites of DEFA5. For example, the antibody may be at least 75%, 80%, 85%, 90%, 95%, 99%, 99.5%, or 100% identical to a complementary polypeptide sequence to polypeptide sequence of the P, B, and M binding sites of DEFA5.

Some embodiments of the antibody disclosed herein more specifically target DEFA5 than they do other alpha defensins. FIG. 1 illustrates dot blotting of the specificity of commercially available DEFA5 antibodies to purified HD1-HD6 proteins versus a Ponceau S control. As used herein, the term "specificity" or similar terms, used in the context of an antibody with regard to its target, refers to the antibody specifically binding to the target antigen (as opposed to other antigens, such as HD1, HD2, HD3, HD4, and HD6). This higher DEFA5 specificity of the present antibody would allow, for example, easier and more accurate testing of DEFA5 levels or expression in samples from subjects.

It is believed that there may be a dysfunction in the activation pathway of DEFA5 in patients suffering from moderate and severe CD, and thus, an excess amount of inactive form DEFA5 is a potential mechanism for inflammation in patients suffering from CD. This excessive amount of inactive form DEFA5 may cause increased damage to the epithelial lining and potentially even a dysregulation in the levels and make-up of gut flora.

The methods may include a step of comparing the level of the DEFA5 to a benchmark value. The benchmark value may be a measure of central tendency based on levels observed in one or more populations of subjects that are established to be unafflicted by either UC or CD. For example, the benchmark value may be a mean level of the gene expression or protein concentration observed in samples from a population of subjects who are unafflicted by UC, unafflicted by CD, or both. The population may be defined by one or more of the patient's geography, age, ethnicity, sex, and medical history. The benchmark value may take into account a measure of variation combined with a measure of central tendency. For example, the benchmark value may be a mean level of the gene expression or protein concentration observed in a given tumor population, plus or minus a margin of error. The benchmark may be based on raw measurements (such as fragments of mRNA or cDNA per kb gene length per million reads) or normalized measurements (such as % of normal expression, or expression compared to a constitutively expressed or widely expressed gene with generally consistent expression, such as β-actin). An example of a suitable benchmark value is about 1 ng/mL DEFA5 or exactly 1 ng/mL DEFA5.

The benchmark may also be established by analysis of a control sample that is measured alongside the sample from the subject. Examples of suitable control samples are: a sample from a subject unafflicted with UC, a sample from a subject unafflicted with CD, a sample from a subject afflicted with UC (although unafflicted with CD), a sample from a subject afflicted with CD (although unafflicted with UC), a sample from a subject afflicted with diverticulitis (although unafflicted with either UC or CD), and a sample from a subject unafflicted from IBD. In some embodiments, the benchmark value level may be a normal level, such as described, infra.

In an embodiment, an assay method of differentially diagnosing UC and CD in a patient suffering from IBD includes measuring the level of DEFA5 or DEFA5 expression present in a sample obtained from the patient. The level of DEFA5 or MMP-7 concentration or expression in the tissue may be measured by any suitable peptide analysis. For example, the measuring step may include one or more of enzyme-linked immunosorbent assay (ELISA), cation-ion exchange, NMR analysis, genome-wide transcriptome analysis, and mass spectrometry. The method may include comparing the concentration or expression of DEFA5 in the sample to the benchmark, and making a diagnosis if the concentration or expression of DEFA5 in the sample is significantly less than or significantly greater than the benchmark value. For example, the method may comprise comparing the concentration or expression of DEFA5 in the sample to the benchmark, and making a diagnosis of CD if the concentration or expression of DEFA5 in the sample is significantly greater than the benchmark value. As another example, the method may comprise comparing the concentration or expression of DEFA5 in the sample to the benchmark, and making a diagnosis of UC if the concentration or expression of DEFA5 in the sample is not significantly greater than the benchmark value. The measurement of the expression of DEFA5 or the concentration of DEFA5 in the sample may be measured in the same ex vivo or in vitro.

The difference in expression or concentration may be considered significant based on any of a variety of known statistical tests for significance. These are generally based on a collection of measurements made from a sampled population, and are affected by both the population size and the sampling size. Such statistical tests are well known in the art and are not further elaborated upon in this disclosure; outside references can be relied upon to enable those skilled in the art to determine statistical significance, such as Rosener's *Fundamentals of Biostatistics*, $8^{th}$ ed. (2015), Cengage Learning, Boston, MA.

In an embodiment, an assay method of differentially diagnosing UC and CD in a patient suffering from IBD includes measuring the level of DEFA5 or DEFA5 expression present in a sample obtained from the patient. The level of DEFA5 or DEFA5 expression in the tissue may be measured by an enzyme-linked immunosorbent assay (ELISA) that uses the targeted DEFA5 antibody disclosed herein. The method includes diagnosing the patient as having UC if DEFA5 or DEFA5 expression is at any level that is indicative of a patient not having CD, such as less than 5× normal levels of DEFA5, or from less than about 5×-30× normal levels of DEFA5 or DEFA5 expression. In an embodiment, the patient is diagnosed as having UC if DEFA5 expression is at a level of less than $3 \times 10^6$ DEFA5 mRNA Transcript per 10 ng RNA. The diagnosing may diagnose the patient as having CD if the level of DEFA5 expression is at any level indicative of a patient having CD, such as from about $3 \times 10^6$ to $1.2 \times 10^8$ DEFA5 mRNA Transcript per 10 ng RNA. As used herein, a "normal level" of DEFA5 or DEFA5 expression means a level of DEFA5 or DEFA5 expression in the digestive tract tissue from a subject not having CD or UC, or a subject suffering from IBD and specifically UC. Normal DEFA5 expression may refer to from $1 \times 10^5$ to $9 \times 10^5$ DEFA5 mRNA Transcript per 10 ng RNA, or about $6 \times 10^5$ DEFA5 mRNA Transcript per 10 ng RNA.

In one embodiment, the assay methods involve determining the status of a subject with respect to the activity and/or expression of DEFA5 or the activity and/or expression of a polypeptide regulated by DEFA5. In one embodiment, such methods comprise determining the level of expression or activity of DEFA5 or a polypeptide regulated by DEFA5 in a sample from the subject with the targeted DEFA5 antibody disclosed herein. The method may further comprise collecting the sample from the subject. As used herein, a biological sample which is subjected to testing is a sample derived from a subject and includes, but is not limited to, any biological material, such as a bodily fluid. Examples of bodily fluids include, but are not limited to, whole blood, serum, saliva, tissue infiltrate, pleural effusions, lung lavage fluid, bronchoalveolar lavage fluid, and the like. The biological fluid may be a cell culture medium or supernatant of cultured cells. For example, the sample can be intestinal tissue, stool, blood, or serum. In embodiment, the biological sample is collected from the colon of a subject.

Some embodiments of the method comprise measuring the concentration of DEFA5 by selectively staining or dying the sample from the subject and measuring the signal from the stain. The stain or dye may comprise the any anti-DEFA5 antibody disclosed herein. The stain or dye may also comprise a reporter, such a colorimetric group, a radionuclide, a stable isotope, a fluorophore, a chromophore, an enzyme, a magnetic particle, and a quantum dot. The concentration of DEFA5 can then be measured by observing the signal from the reporter, such as by microscopy, colorimetry, radiometry, fluoroscopy, magnetotaxis, or any combination of the foregoing. In a specific embodiment of the method, the concentration of DEFA5 is measured by immunostaining the sample with an immunostain that recognizes DEFA5 and counting the number of stained cells by microscopy. This approach has the advantage of relative simplicity, and only requires the types of equipment that are already present in typical clinical laboratories. A diagnosis can be made based on a threshold number of cells that stain positive, such as at least 10%, 20%, and 30%. If the number of DEFA5 stained cells is significantly above the threshold value, than a diagnosis of CD can be made; whereas if the number of DEFA5 stained cells is significantly below the threshold value, than a diagnosis of UC can be made.

Those subjects in which DEFA5 activity and/or expression differs (increased or decreased) from a control or benchmark value or the activity of a polypeptide regulated by DEFA5 differs as compared to a control or benchmark value are determined to be suffering from or at risk for disease states and conditions associated with or characterized by increased or decreased DEFA5 activity.

Assay techniques that can be used to determine levels of expression or activity in a sample are known. Such assay methods include, but are not limited to, radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Assays also include, but are not limited to, competitive and non-competitive assay systems using techniques such as radio-immunoassays, enzyme immunoassays (EIA), enzyme linked immunosorbent assay (ELISA), sandwich immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. For examples of immunoassay methods, see U.S. Pat. Nos. 4,845,026 and 5,006,459. Any of the anti-DEFA5 antibodies disclosed herein may be in the assay.

The anti-DEFA5 antibody can be incorporated into an ELISA assay for the diagnosing methods. In addition, a reporter antibody generally is prepared. The reporter antibody is attached to a detectable reagent such as a radioactive, fluorescent, or enzymatic reagent, for example horseradish peroxidase enzyme or alkaline phosphatase. In one embodiment of the ELISA, to carry out the ELISA, the anti-DEFA5 antibody is incubated on a solid support that binds the antibody. Any free protein binding sites on the dish are then covered by incubating with a non-specific protein. Next, the sample to be analyzed is incubated with the solid support, during which time the anti-DEFA5 antibody binds to DEFA5. Unbound sample is washed out with a buffer. A reporter antibody specifically directed to the antigen and linked to a detectable reagent is introduced resulting in binding of the reporter antibody to any antibody bound to the antigen. Unattached reporter antibody is then washed out. Reagents for detecting the presence of the reporter antibody are then added. The detectable reagent is then determined in order to determine the amount of antigen present. In an alternate embodiment, the antigen is incubated with the solid support, followed by incubation with one or more antibodies, wherein at least one of the antibodies comprises a detectable reagent. Quantitative results may be obtained by reference to a standard curve.

A method of treating IBD in a patient suffering from IBD may include: (a) measuring the level of DEFA5 or DEFA5 expression present in a sample obtained from the patient with the anti-DEFA5 antibody, whereby a level of DEFA5 or DEFA5 expression is obtained; (b) if the level of DEFA5 or DEFA5 expression is at a level indicative of a patient not having CD, treating the IBD in the patient with a suitable medical treatment for UC; if the level of DEFA5 or DEFA5 expression is at a level indicative of a patient having CD, treating the IBD in the patient with a suitable medical treatment for CD.

Suitable medical treatments for UC include ileal pouch anal anastomosis or the administration of pharmaceutical agents or salts thereof. Suitable pharmaceutical agents may be one or more of: an iron supplement; an oral 5-aminosalicylate, such as mesalamine, balsalazide and olsalazine; an anti-inflammatory; a corticosteroid; an immunosuppressant such as azathioprine, mercaptopurine, methotrexate, and cyclosporine; an anti-TNF-alpha antibody such as infliximab, adalimumab, and golimumab; an anti-α4-integrin antibody such as vedolizumab; and an antibacterial antibiotic such as ciprofloxacin and metronidazole. Surgeries that are sometimes used to treat UC include a total proctocolectomy, and an ileal pouch anal anastomosis. Note that ileal pouch anal anastomosis are recognized as relatively ineffective when used to treat CD, in contrast to UC. It should also be noted that cyclosporine and golimumab, while currently approved for the treatment of UC in the United States, are not currently approved for the treatment of CD. Some embodiments of the method involve performing an intervention that is effective to treat UC, but either ineffective to treat CD or not yet approved by regulatory authorities for the treatment of CD.

Suitable medical treatments for CD include the administration of pharmaceutical agents or salts thereof. Suitable pharmaceutical agents include: an oral 5-aminosalicylate, such as mesalamine; a vitamin supplement, such as a vitamin B-12 supplement and a vitamin D supplement; a mineral supplement, such as a calcium supplement; an anti-inflammatory; a corticosteroid such as prednisone and budesonide; an immunosuppressant such as azathioprine, tacrolimus, methotrexate, and mercaptopurine; an anti-TNF-α antibody, such as infliximab, adalimumab, and certolizumab pegol; an anti-α-4-integrin antibody, such as natalizumab and vedolizumab; an anti-interleukin antibody, such as ustekinumab; and an antibacterial antibiotic, such as metronidazole, and ciprofloxacin. Although certolizumab pegol, methotrexate, and natalizumab are approved in the US for the treatment of CD, they are not currently approved for the treatment of UC. Surgical approaches are sometimes used to treat severe cases of CD. Such surgeries include ostomy, colostomy, ileostomy, bowel resection, colectomy, proctocolectomy, and strictureplasty. In some embodiments of the method, the subject is treated using a diet that is advantageous for the management of CD, but not necessarily advantageous in the management of UC. One such diet is a low fat diet. Some embodiments of the method involve performing an intervention that is effective to treat CD, but either ineffective to treat UC or not yet approved by regulatory authorities for the treatment of UC. The intervention may be administration of a drug, to the exclusion of a surgery. The administration of a drug may be administration of a drug selected from the group consisting of: a vitamin supplement, an anti-inflammatory, a corticosteroid, prednisolone, methyl-prednisolone, oral budesonide, a 5-aminosalicylate, an immunosuppressant, azathioprine, mercaptopurine, an anti-TNF-alpha antibody, infliximab, adalimumab, certolizumab pegol, methotrexate, an anti-α4-integrin antibody, natalizumab, vedolizumab, an anti-interleukin antibody, ustekinumab, an antibacterial antibiotic, ciprofloxacin, metronidazole, an anticholinergic agent, propantheline, dicyclomine, hyoscyamine, a bile acid sequestrant, cholestyramine, colestipol, and colesevalm. The administration of a drug may be administration of a drug, vitamin, or mineral selected from the group consisting of: vitamin B12, vitamin D, calcium, certolizumab pegol, methotrexate, and natalizumab. The intervention may be enteral nutrition therapy, including elemental and non-elemental diets, such as by nasogastric tube feeding. In an embodiment, the level of DEFA5 or DEFA5 expression may be elevated above normal levels in patients who are likely to be diagnosed UC but, at the time the DEFA5 or DEFA5 expression level is measured, diagnosed as having IC. These patients may be treated with any suitable medical treatments for UC. The intervention may be placing the subject on a low fat diet or a high fiber diet.

The intervention suitable for UC may be administration of a drug selected from the group consisting of: an iron supplement, an anti-inflammatory, a corticosteroid, hydrocortisone, cortisone, prednisolone, a 5-aminosalicylate, an immunosuppressant, azathioprine, mercaptopurine, cyclosporine, an anti-TNF-alpha antibody, infliximab, adalimumab, golimumab, methotrexate, an anti-α4-integrin antibody, vedolizumab, an antibacterial antibiotic, ciprofloxacin, metronidazole, suppository mesalazine, enema mesalazine, olsalazine, balsalazide, enema budesonide, tacrolimus, and a combination of any of the foregoing. The intervention suitable for UC may be administration of a drug selected from the group consisting of: cyclosporine, and golimumab.

A kit is provided for measuring DEFA5 in a subject. The kit may find use in several of the methods provided above, as well as others. The kit may be, for example, used for the diagnosis of inflammatory bowel disease. The kit comprises an assay for measuring at least one of DEFA5 concentration and DEFA5 expression. The kit may include an assay comprising an anti-DEFA5 antibody; and a sample container configured to contain a sample selected from: a stool sample, a blood sample, a bowel tissue sample, and a serum sample. The first assay may include a sample collector selected from the group consisting of: a stool sample collector, a blood sample collector, a serum sample collector, and a bowel tissue collector.

FIG. 1 illustrates dot blotting of the specificity of commercially available DEFA5 antibodies to purified HD1-HD6 proteins versus a Ponceau S control. It is believed that the targeted DEFA5 antibody of the present embodiments has a higher specificity than these commercially available antibodies such that, for example, purification of DEFA5 in samples would not be required or be minimal. As used herein, the term "specificity" or similar terms, used in the context of an antibody regarding to its target, refers to the antibody specifically binding to the target antigen (as opposed to other antigens, such as HD1, HD2, HD3, HD4, and HD6). This higher DEFA5 specificity of the present antibody would allow, for example, easier and more accurate testing of DEFA5 levels or expression in samples from subjects.

Figure 3:
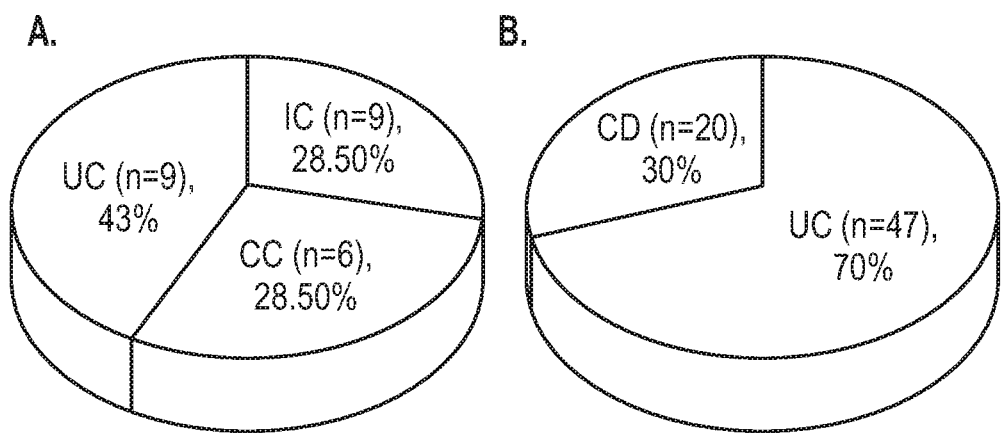
FIG. 3A shows initial diagnostic information of 21 subjects diagnosed with ulcerative colitis, indeterminate colitis, or Crohn's disease.
FIG. 3B shows diagnostic information of the 21 subjects reevaluated 9.4 years after the initial diagnostic information of FIG. 3A.

FIG. 2A illustrates an alignment of the primary sequence of DEFA5 with that of HD1 and HD6. FIG. 2B is a schematic showing DEFA5 antibody epitopes to distinguish pro-DEFA5 from mature protein in sera of IBD patients. FIG. 2C is a model of sandwich ELISA to be used to detect pro-DEFA5 and mature DEFA5 in sera of IBD patients. FIGS. 3A and 3B illustrate the problem of diagnostic uncertainty and inaccuracy in IBD clinical setting. FIG. 3A shows that twenty-one IC patients were followed for approximately ten years. At the end of the 10 year period, 28.5% of the patients could still not be delineated into a precise diagnosis of either UC or CC. FIG. 3B shows sixty-seven UC RPC operated patients that were followed for re-evaluation after a mean follow-up of 9.4 (range, 8-13) years after operation. Thirty percent of these patients required a change of diagnosis to de novo Crohn's disease.

FIGS. 4A-4D show that DEFA5 levels can be used to determine patient candidacy for IPAA. FIG. 4A shows representative results from a RPC-operated patient that did not change the diagnosis after surgery and was molecularly tested using DEFA5 IHC. FIG. B shows representative results from a UC RPC and IPAA operated patients that did change the diagnosis from UC to de novo Crohn's was molecularly tested using DEFA5 IHC. FIG. 4C shows NL-Ileum, control. FIG. 4D shows quantification of NEARAS DEFA5 IHC staining spot counts for UC RPC and IPAA-operated patients who did not have their original diagnosis changed versus those who did change from UC to de novo Crohn's. (Ctrl 1—staining control, UC—Ulcerative Colitis, CC—Crohn's Colitis, DV—Diverticulitis, DVL—Diverticulosis).

Figure 5:
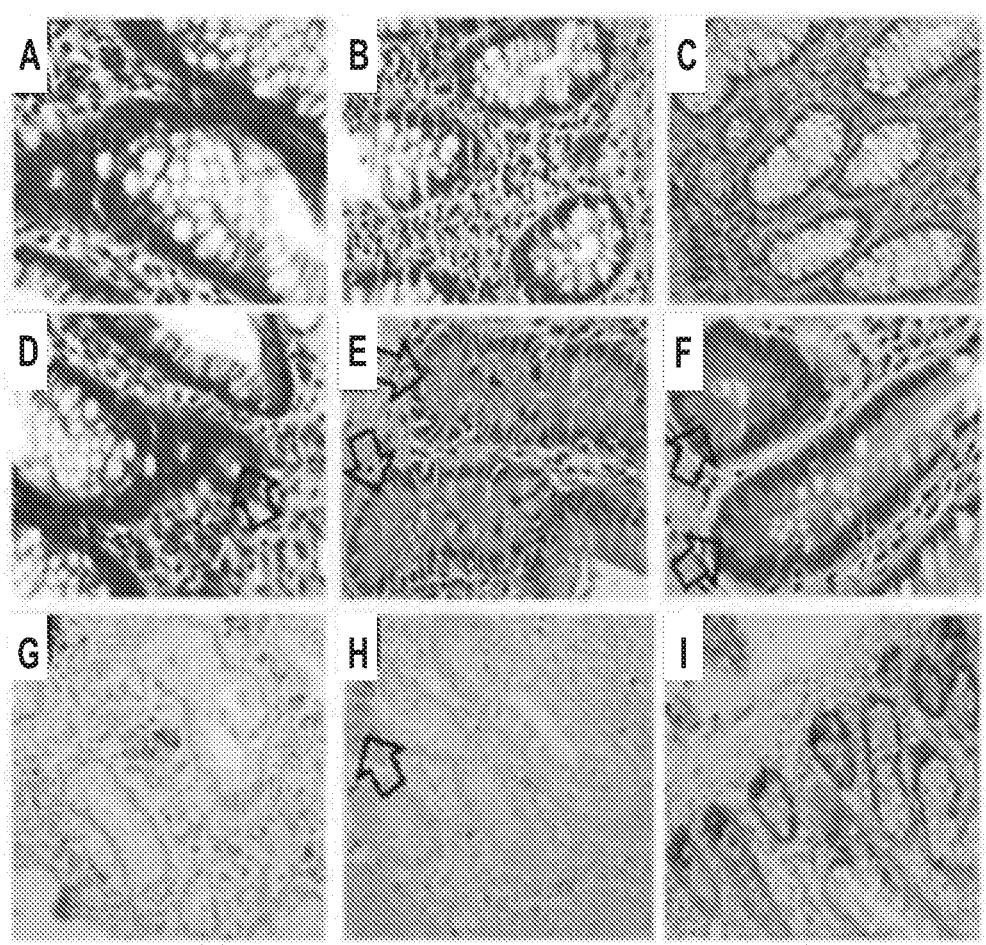
FIGS. 5A-5I illustrate histological staining on parallel sections for the typical morphological appearance of Paneth cell (PCs) including the presence of dense apical eosinophilic granules.

FIGS. 5A-5I illustrate histological staining on parallel sections for the typical morphological appearance of Paneth cell (PCs) including the presence of dense apical eosinophilic granules. Upper panel: FIG. 5A, Diverticulitis (DV, no PCs), FIG. 5B, Diverticulosis (DVL, no PCs), FIG. 5C, Normal (NL-Colon, Control, no PCs). Middle panel: FIG. 5D, UC (found prodromal PC in one patient, arrow). FIG. 5E, CC, demonstrate abundance of PCs allover colonic basal crypts (arrows). FIG. 5F, Normal (NL-Ileum, Control), with abundance of PCs. Lower panel: IHC detection of Paneth cell markers α-defensin 5 (DEFA5) and lysozyme (LYZ) in the colon. FIG. 5G, NL-Colon, FIG. 5H, CC, and FIG. 5I, NL-Ileum, Control.

Figure 6:
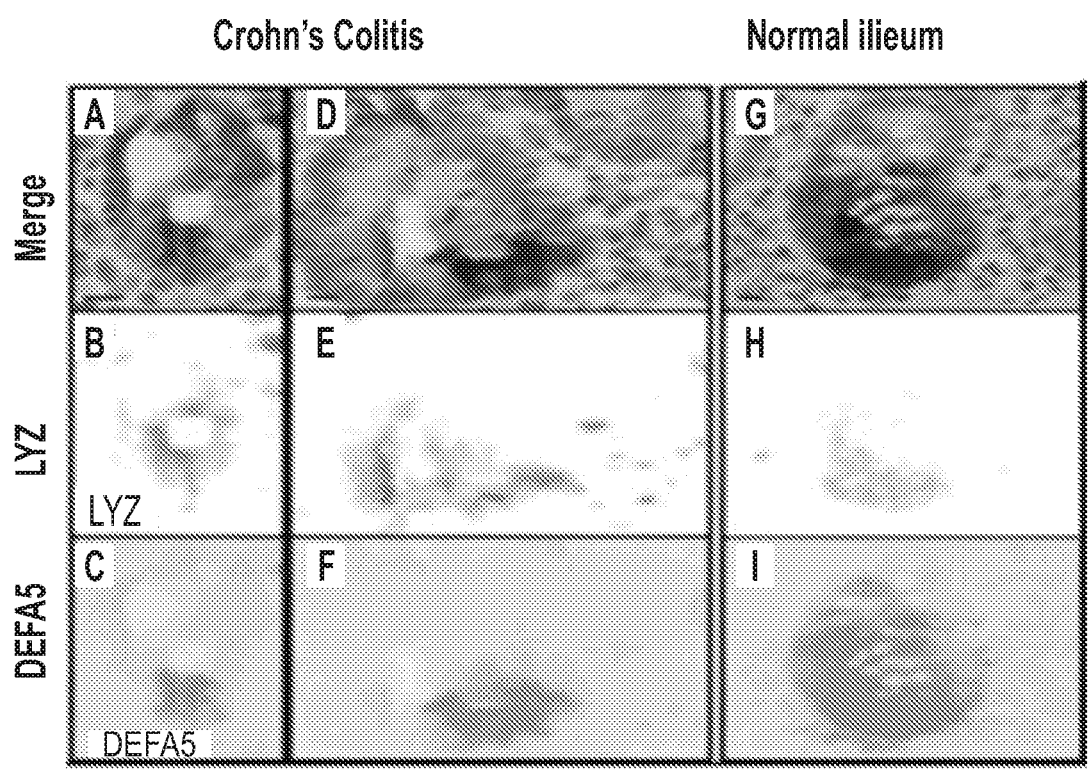
FIGS. 6A-6J illustrate a double histological stain of PCs, lysosomes, and DEFA5.

FIGS. 6A-6J illustrate H&E staining on parallel sections for the typical morphological appearance of Paneth cell (PCs) including the presence of dense apical eosinophilic granules. Upper panel: FIG. 6A, Diverticulitis (DV, no PCs), FIG. 6B, Diverticulosis (DVL, no PCs), FIG. 6C, Normal (NL-Colon, Control, no PCs). Middle panel: FIG. 6D, UC (found prodromal PC in one patient, arrow). FIG. 6E, CC, demonstrate abundance of PCs allover colonic basal crypts (arrows). FIG. 6F, Normal (NL-Ileum, Control), with abundance of PCs. Lower panel: IHC detection of Paneth cell markers α-defensin 5 (DEFA5) and lysozyme (LYZ) in the colon. FIG. 6G, NL-Colon, FIG. 6H, CC, and FIG. 6I, NL-Ileum, Control.

Figure 7:
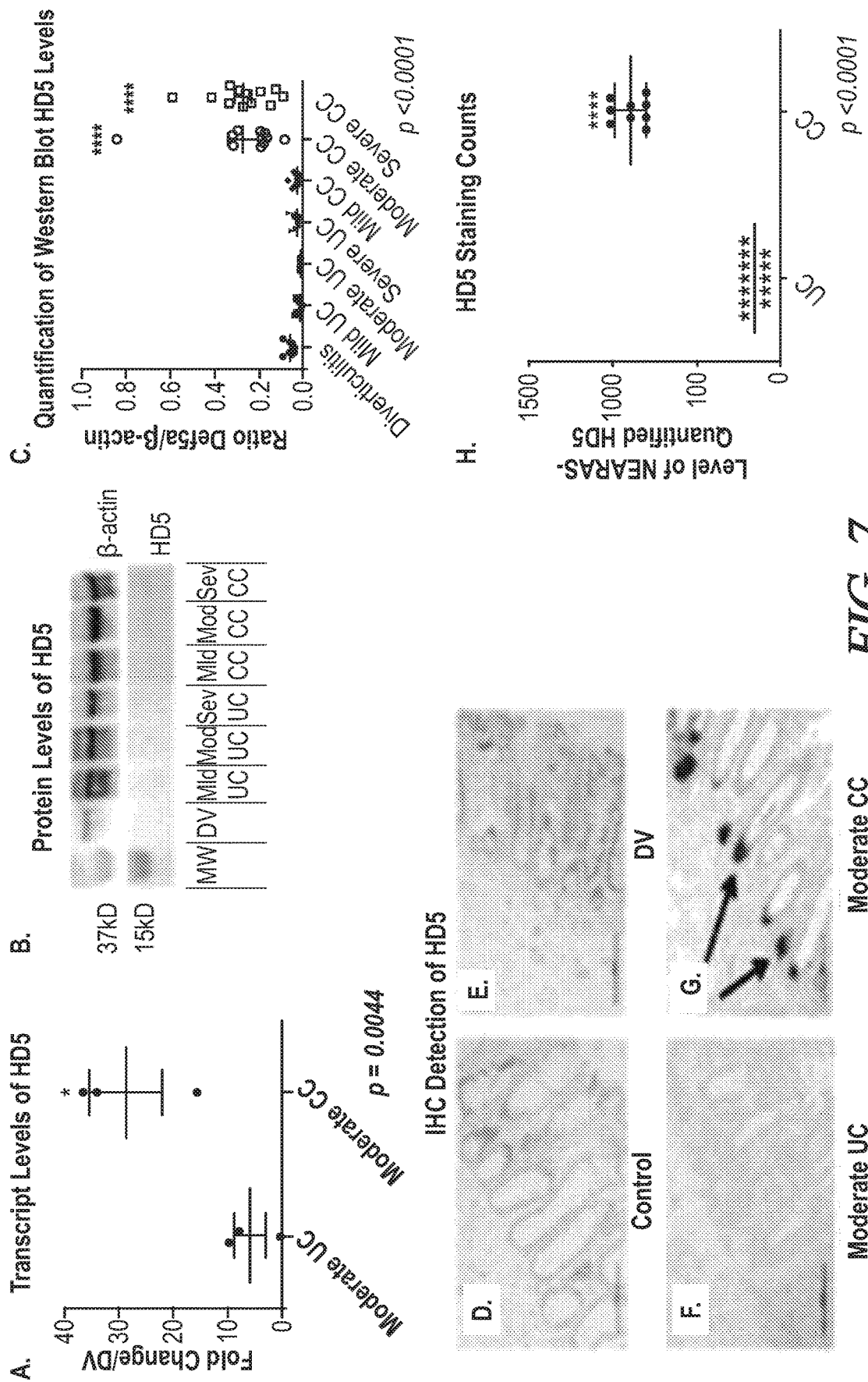
FIG. 7A illustrates quantification of DEFA5 transcript levels in moderate UC and CC samples.
FIG. 7B illustrates a DEFA5 western blot showing higher DEFA5 levels in moderate and severe CC compared to other IBD disease states.
FIG. 7C illustrates DEFA5 levels in various IBD disease states.
FIGS. 7D-7H illustrate IHC staining of DEFA5 in colonic tissues using formalin-fixed paraffin-embedded thin sections.

FIGS. 7A-7J show a double stain of PCs, Lysosomes and DEFA5. Double staining analyses from de novo Crohn's (FIGS. 7A and 7D), and normal ileum/control (FIG. 7G) are illustrated. Image deconvolutions are displayed vertically to evaluate lysozyme specific permanent red (FIGS. 7B, 7E, and 7H) and DEFA5α-specific DAB (FIGS. 7C, 7F, and 7I). The normal colon image (FIG. 7J), which lacks PCs, was not further processed by double staining.

Working Example 1

Working Example 1 shows that human UC and CC can be distinguished molecularly by examining DEFA5 levels in colectomy tissues, colon biopsies, and/or sera in humans using the DEFA5 antibodies described herein. Also, Working Example 1 delineates the underlying mechanisms for the subtle differences between UC and CC. The ability to accurately distinguish CC from UC is significant and of clinical importance, and is especially meaningful for gastroenterologists and colorectal surgeons, particularly before deciding whether restorative proctocolectomy surgery is required in a patient having IBD.

Methods

The inability to accurately distinguish Crohn's disease (CC) from UC leads to an inexact diagnosis denoted as IC, which greatly affects the medical and surgical care of the patients. A preliminary assessment of DEFA5 expression was performed in a pilot cohort of IC patients as well as in UC patients who underwent RPC surgery. This showed that DEFA5 levels and to a lesser extent DEFA6 levels were higher in CC patient samples. The preliminary data reveal that detection of DEFA5 in the tissues of the IC patients or those from the RPC surgery UC patients, who in fact were CC, were more accurately differentiated CC from UC in then otherwise misdiagnosed patients.

Clinical Samples.

Figure 11:
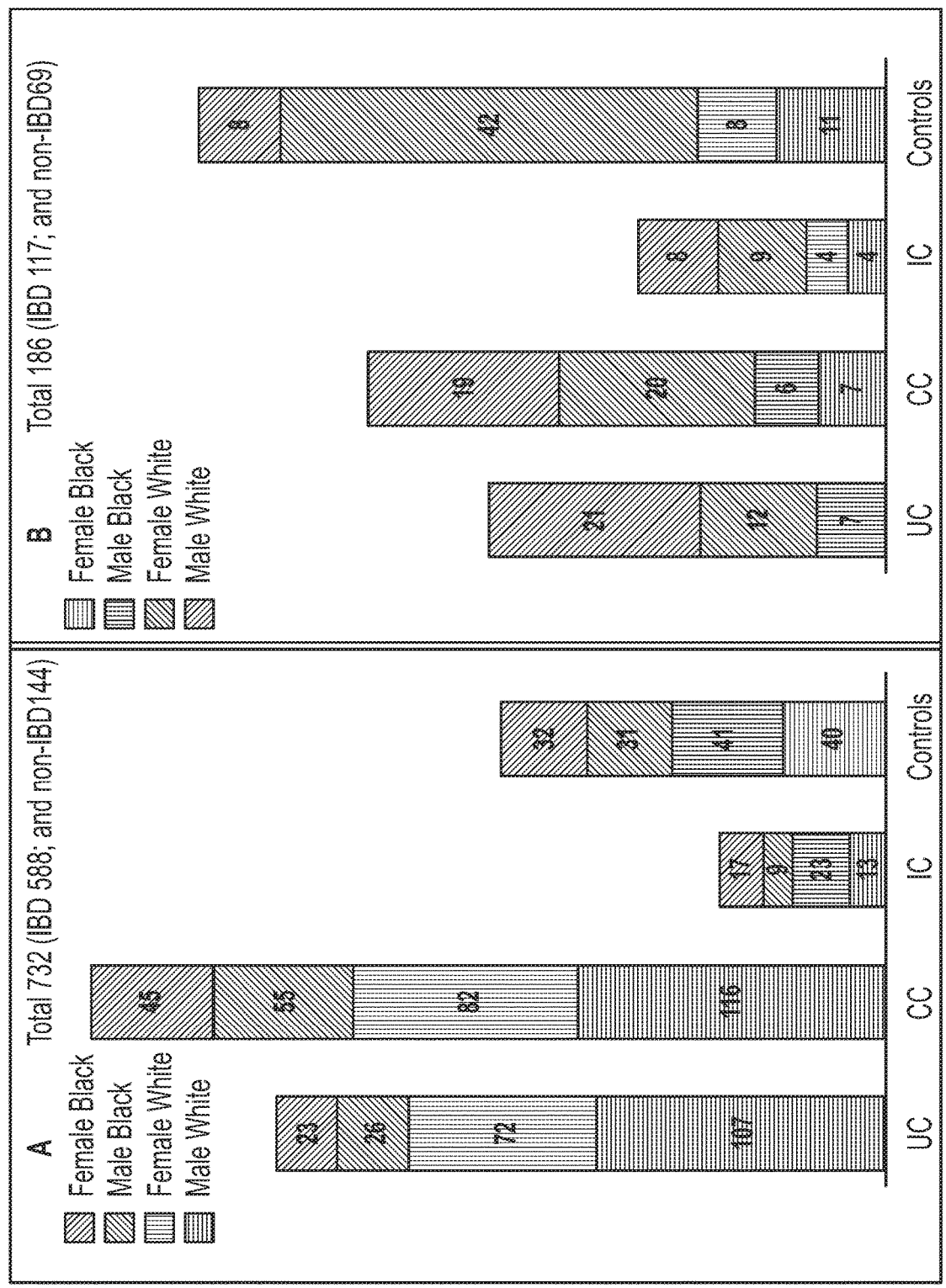
FIGS. 11A and 11B illustrate the distribution of collected fresh frozen tissue and blood samples from IBD and non-IBD patients by sex and race.

To show that aberrant DEFA5 expression in IBD patients is a more reliable diagnostic approach to differentiate CC from UC, the potential of detection of DEFA5 as a biomarker for CC in IBD patient samples diagnosed as UC, CC and IC tissues was explored. FIGS. 11A and 11B illustrate a distribution of collected fresh frozen tissue and blood samples from IBD and none-IBD patients by sex and race. FIG. 11A illustrates a categorization of tissue samples by female, male, white, and black shows tissue samples (732 samples) and FIG. 11B illustrates a categorization of sera samples (186 samples) as female, male, white, and black. The samples were stored at −80° Celsius. The patient samples diagnosed as UC, CC, and IC tissues were subjected to immunohistochemistry (IHC) and semi-quantitative RT-PCR to evaluate the potential for detection of DEFA5 as a biomarker for CC in IBD patient samples diagnosed as UC, CC and IC tissues. A total of 732 tissues and 186 sera from IBD and healthy individuals distributed by race and gender were collected, as depicted in FIGS. 11A and 11B. The tissues were surgical colectomy tissues from consented adults with definitive and unambiguous diagnoses of UC and CC as well as from those diagnosed with IC at Vanderbilt University Medical Center (VUMC). The collection of these patient samples was approved by Meharry Medical College (MMC) and VUMC IRB Committees. The full thickness of the tissues was analyzed by pathology teams at MMC and VUMC following established criteria for IBD subtypes. For each sample, medical data pertaining to patient demographics, variables prior to and after surgery, surveillance endoscopic and clinical findings, and medical and surgical treatment history were reviewed retrospectively. The experimental samples were taken from various parts of the colon.

Clinical Retrospective Studies on IBD Patients Reveal Persistent Diagnostic Uncertainty.

A retrospective investigation was conducted on a cohort of 21 patients diagnosed with IC between 2000 and 2007 at the IBD Center at VUMC, with a mean follow-up period of 8.7±3.7 (range, 4-14) years. In 2014, these patients were re-evaluated to determine whether the diagnosis resolved to UC or CC. Three GI pathologists blinded to the initial clinical outcome re-evaluated each patient and the new diagnosis was presented as a consensus among the attending physicians. The pathology reevaluations concluded that the diagnosis of 6 patients, (28.5%) remained as IC because these could still not be delineated into UC or CC. Meanwhile 43% and 28.5% resolved into UC and CC respectively (FIG. 3A). In another retrospective study, 120 patients with "definitive" UC underwent RPC with IPAA surgery between 2001 and 2008. Of the 120 patients, 67 had their diagnosis reevaluated after a mean follow-up period of 9.4 (range, 8-13) years with functionally acceptable pouches. As shown in FIG. 3B, 30% of the initial UC diagnosis changed to de novo Crohn's disease (de novo CD). Together, this emphasizes the persistent diagnostic uncertainty of the at least 30% of IBD cases and more so the need for more reliable diagnostic procedures.

Differential Expression of DEFA5 in CC and UC.

Two approaches were used, training and Independent test sets, to identify genes or their products that are differentially expressed in UC versus CC. In a training test set, a whole-transcriptome microarray was performed using RNA extracted and pooled from full-thickness colon samples from UC and CC patients (n=5) using the Affymetrix gene expression array according to the manufacturer's instructions (Affymetrix, Santa Clara, CA). Tissues from diverticulitis were used as control. This analysis showed a total of 484 genes that were up- or down-regulated antimicrobial peptides, and mucins between the two diseases. In a test set analysis using microarray technologies (Affymetrix, Santa Clara, CA). DEFA5 levels increased the most: 31-fold in CC vs. UC ($p<7.23E-05$), Table 2. In an independent test set, the gene expression profiling was independently verified using a PCR array (NanoString Technologies Inc., Seattle, WA) that specifically targeted inflammatory genes. It was found that DEFA5 was also increased 118-fold in CC vs. UC ($p<0.001$) in different colon samples from UC and CC patients with same disease activity as in test set. Table 3. The only gene to show up in both the microarray and the PCR array was DEFA5. Among the upregulated genes were α-defensin-5, other antimicrobial peptides, and mucins (Table 2). HD5 was increased the most: 31-fold in CC vs. UC (in a previous test HD5 increase by 118-fold in CC versus UC—Table 3). A full list of the microarray results can be found in Table 2. Table 2 shows a list of targets from an AFFYMETRIX cDNA microarray. A total of 484 genes were highlighted in the microarray as potential markers for distinguishing UC from CC. The gene showing the largest fold change between the two diseases was Human Defensin 5 (HD5).

To further validate these data, DEFA5 expression was assessed by semi-quantitative RT-PCR using RNA extracted from moderate CC and moderate UC tissues (n=3). This analysis confirmed that DEFA5 mRNA levels were significantly higher in CC compared to UC (FIG. 7A, SEM, $p<0.03$). Dot blotting was used to screen commercially available antibodies against recombinant DEFA5 using bacterial lysates prepared from DEFA1-6 transformed bacteria. This led to the discovery of a monoclonal antibody from Santa Cruz Biotechnology, Inc. (Santa Cruz, CA)—α-defensin 5 antibody (catalogue #53997)—as a high specificity and high affinity DEFA5 antibody for use in assays. Next, DEFA5 expression was assessed by western blotting (n≥10 for each disease) (FIG. 7B), and it was found that tissues from moderate and severe CC patients expressed higher levels of DEFA5 compared to those from all other disease states (FIG. 7C, $p<0.0001$). However, because full-thickness samples were used for the western blots, the overall abundance of DEFA5 in the samples was low. Finally, the expression of DEFA5 was examined in moderate IBD and control tissues by IHC using FFPE sections. This analysis also revealed that DEFA5 levels higher in CC tissues (FIG. 7G) than in DV, UC, and normal (NL) control tissues (FIGS. 7D, 7E, and 7F). Quantification of the DEFA5 IHC staining revealed a 5.6-fold increase of DEFA5 in CC vs. UC samples (FIG. 7H, $p<0.0001$). Interestingly, detection of DEFA5 by IHC depicted localized DEFA5 staining in the base of individual colonic crypts. FIGS. 7A-7H show that DEFA is aberrantly expressed in IBD. FIG. 7A shows quantification of DEFA5 transcript levels in moderate UC and CC samples by semi-quantitative RT-PCR confirms higher DEFA5 levels in moderate CC than in moderate UC ($p<0.05$). FIG. 7B is a representative DEFA5 western blot showing higher DEFA5 levels in moderate and severe CC compared to all other IBD disease states. β-actin was used as the loading control. FIG. 7C shows a graphical representation (densitometry) of DEFA5 levels in various IBD disease states. Each dot represents the ratio of DEFA5 to β-actin. Moderate and severe CC levels of DEFA5 are both significantly higher than all other disease states ($p<0.0001$). FIGS. 7D-7H illustrate representative IHC staining of DEFA5 in colonic tissues using formalin-fixed paraffin-embedded (FFPE) thin sections—FIG. 7D shows Diverticulosis, no primary antibody control; FIG. 7E shows moderate diverticulitis; FIG. 7F shows moderate UC; FIG. 7G shows moderate CC; and FIG. 7H shows quantification level of DEFA5 IHC staining in moderate UC vs. moderate CC. Levels of DEFA5 are increased in CC as compared to UC ($p<0.0001$). Magnification of these illustrated tissues is at 40×.

Detection of DEFA5 in IBD Colectomy Tissues Agrees with Follow-Up Clinical Patient Outcomes as a Potentially Selective Diagnostic Tool for CC.

To test if detection of DEFA5 could be used to discriminate CC from UC and if this agreed with the patient follow-up clinical outcomes, detection of DEFA5 was carried out in the tissues from the 21 IC patients (FIG. 3A) by IHC. The staining intensity was evaluated using the Nikon Element Advanced Research Analysis Software (NEARAS). Based on the DEFA5 staining intensity, it was found that among the six patients with unchanged IC diagnoses, and as depicted in Table 1, below, three patients showed high DEFA5 staining and conformed to the final diagnosis for CC (circled below), and three patients showed low DEFA5 staining and conformed to the final diagnosis for UC (circled below).

TABLE 1

| Patient Sample ID | Attending Pathologist Diagnosis Year 2000-2007 | Attending Physician Diagnosis Year 2000-2007 | Patient Outcomes Year 2014 - New Diagnosis | Mean Area Fraction of DEFA5 (%) Count by NEARAS |
|---|---|---|---|---|
| 12-07-A1588 | IC | UC | UC | 20 |
| 12-10-A051A | IC | IC | ⓒⓒ | 80 |
| ED56738T-003 | IC | UC | UC | 10 |
| 2nd Opinion | IC | UC | | |
| ED59253T-003 | IC | UC | UC | 20 |
| 2nd Opinion | IC | UC | | |
| M1122098A2 | IC | IC | ⓤⓒ | 20 |
| M1122098A2 | IC | UC | UC | 10 |
| M3124384A1 | IC | CC | UC | 10 |
| M3124405A2 | IC | CC | CC | 70 |
| 2nd Opinion | IC | UC | | |
| D-24672 | IC | UC | CC | 70 |
| D-4632 | IC | UC | UC | 20 |
| D-3163 | IC | CC | CC | 90 |
| D-26455 | IC | IC | CC | 80 |
| D-26452 | IC | CC | ⓒⓒ | 80 |
| D-325 | IC | UC | UC | 10 |
| D-2462 | IC | CC | CC | 100 |
| A-24057 | IC | UC | UC | 20 |
| A-24066 | IC | CC | CC | 100 |
| A-24042 | IC | IC | ⓤⓒ | 20 |
| 56738T | IC | IC | ⓒⓒ | 100 |
| MAD12-625 | IC | IC | ⓤⓒ | 10 |
| M1151537AA | IC | UC | UC | 20 |

Figure 4:
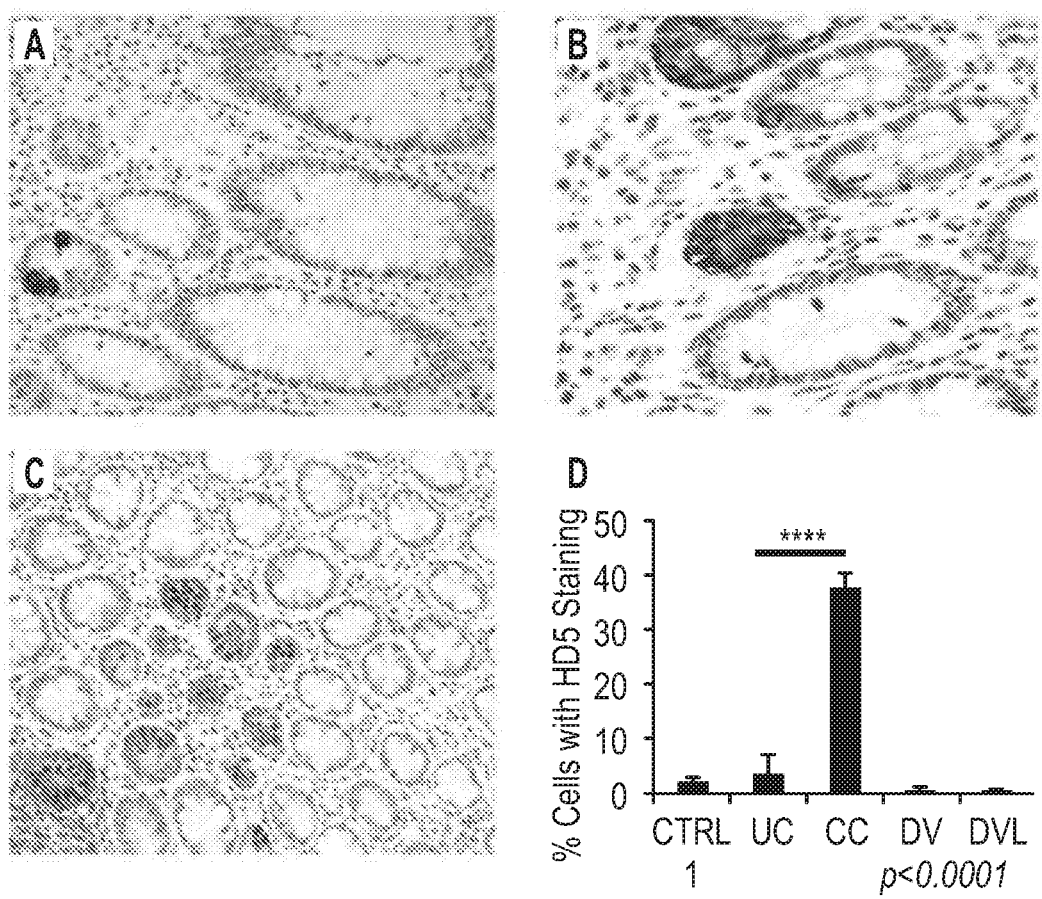
FIGS. 4A-4C are histological staining of DEFA5 tissue samples from patients treated with various treatments.
FIG. 4D is a quantification of staining spot counts for ulcerative colitis RPC and IPAA-operated patients who did not have their original diagnosis changed versus those who did change from ulcerative colitis to de novo Crohn's disease.

DEFA5 staining was also evaluated for the RPC and IPAA-operated patients described in FIG. 3B who had a clinical change in diagnosis to de novo CD (n=20) and those whose diagnoses did not change (n=47). FIG. 4 illustrates how DEFA5, as disclosed herein, is a tool for determining patient candidacy for IPAA. FIG. 4A shows colectomy tissue from an RPC-operated patient whose diagnosis did not change. The tissue was molecularly tested using DEFA5 IHC. FIG. 4B shows colectomy tissue from a UC RPC and IPAA-operated patient whose diagnosis changed from UC to de novo CD. The tissue was molecularly tested using DEFA5 IHC. FIG. 4C shows NL-Ileum, control. FIG. 4D shows quantification to compare NEARAS DEFA5 IHC staining in tissues from UC RPC and IPAA-operated patients whose original diagnoses did not change vs. those whose diagnoses changed from UC to de novo CD (FIG. 11B). (Ctrl 1—control, UC—Ulcerative Colitis, CC—Crohn's Colitis, DV—Diverticulitis, DVL—Diverticulosis). The DEFA5 IHC revealed that patients whose diagnosis remained unchanged i.e. UC, showed only trace levels of DEFA5 (FIGS. 4A and 4D) while those whose diagnoses clinically changed from UC to de novo CD showed significantly strong (p<0.0001) DEFA5 staining (FIGS. 4B and 4D). As expected, DEFA5 staining in normal ileum control tissues was high (FIG. 4C). Statistical analysis to determine positive predictive values (PPVs) of DEFA5 in patient tissues showed 95.8% for CC and only 76.9% for UC. Chi squared analysis shows significant relatedness between high levels of DEFA5 and a CC diagnosis (p<0.0001). These data indicate that DEFA5 is a candidate diagnostic marker to accurately distinguish CC from UC and to reliably reclassify IC into the CC and UC subtypes.

Establish the Specificity, and Selectivity of DEFA5 Antibodies.

Figure 10:
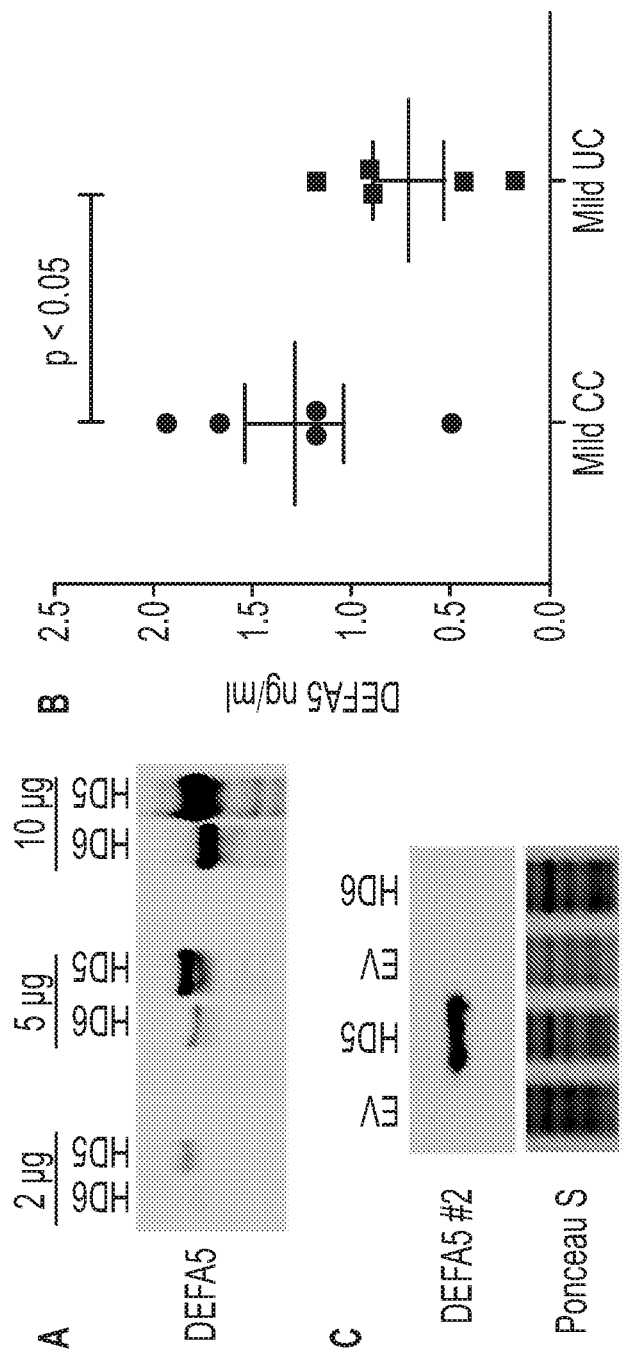
FIGS. 10A-10C illustrate detection of DEFA5 in IBD patient sera and specificity of available DEFA5 antibodies.

Although the detection of DEFA5 in IBD tissues by IHC (FIGS. 4A-4D) is consistent with the RT-PCR data (FIGS. 7A-7H), the commercially available antibodies may exhibit some cross reactivity, especially with PC derived DEFA6. This led us to evaluate commercially available DEFA5 antibodies by dot blotting. A DEFA5 antibody from Santa Cruz Biotechnology (α-defensin 5 antibody catalog number sc-53997) was identified as a DEFA5 specific antibody. An evaluation of the antibody for cross-reactivity with DEFA6 revealed that this antibody strongly detected DEFA5 and to a lesser extent DEFA6 (FIG. 10A). Given the possibility that antibodies to these proteins may cross-react, it was sought to identify DEFA5 specific antibodies. A total of 11 monoclonal antibodies to DEFA5 were obtained from R&D Systems and their ability to be used as specific DEFA5 detection antibodies was evaluated (FIG. 10C). A DEFA5 sandwich ELISA kit (OKEH01234) was obtained from AVIVA System Biology Inc. to determine whether DEFA5 can be detected in patient sera. Surprisingly, DEFA5 was detected in sera from profiled patients with mild CC and mild UC activity and found that DEFA5 was higher in sera from CC than in UC patients, p<0.05; R2=0.9938 (FIG. 10B).

Prophetic Example 2

Establish the Specificity, and Selectivity of DEFA5 Antibodies for Sandwich ELISAs.

It is believed that the specificity of the commercially available ELISA kit can be determined by using DEFA6 as the antigen. If test proves to be not specific, it is believed that immunoprecipitations (IPs) using DEFA5 and DEFA6 expressed in bacteria and the 11 monoclonal antibodies to DEFA5 can identify those that may specifically form immune complexes with DEFA5 but not DEFA6 can be conducted. It is believed that a R&D Systems DEFA5 antibody (catalogue number 972207.111 or CSL 1450400) from R&D SYSTEMS, Minneapolis, MN, can be biotinylated and used as the detection antibody for the IPs. It is believed that the combination of the detection and the best capture antibodies to develop a more specific sandwich ELISA to detect DEFA5 in sera. Overall, it is believed that purified DEFA5 expressed in bacteria can be used to determine the appropriate concentrations of the DEFA5 antibodies for a robust ELISA and compare this with the commercially available ELISA kits.

Optimize the DEFA5 Sandwich ELISA to Detect DEFA5 in Sera from IBD Patients and Normal Subjects.

Since DEFA5 has not been used in IBD clinical settings, the goal of this task will be to establish normal blood DEFA5 reference interval levels and compare these to the values in sera of IBD patients. As depicted in FIG. 10B, it is envisioned that DEFA5, a protein produced locally at the intestinal mucosal crypt, can be detected in circulating human sera by sandwich ELISA. Sera from 117 IBD patients (40

UC, 52 CC, and 25 IC) and 69 non-IBD controls across different race/ethnicities and both genders (FIG. 11B) has been collected. A sample size of 92 subjects, (46 CC and 46 UC) will be used to detect a clinically significant difference of 19% between the positive predictive values of CC and UC using a one-tailed test of proportions between the two groups with 80% statistical power and a 5% level of significance. This 19% difference represents a 96% probability that subjects in CC group with a positive screening test truly have the disease and the 77% positive predictive value for subjects in UC group. To establish normal values of DEFA5 in human sera, up to 120 sera from males and a similar number from females with varied ethnic backgrounds, from outpatient clinics at MMC and VUMC will be used. Sera will be disqualified from those who have been diagnosed with diseases that may impact the analysis. Pre-analytical sampling and quantitative analysis will be performed, as well as the definition, establishment, and verification of DEFA5 reference intervals according to previously established guidelines. Blood samples from healthy individuals at VUMC Clinical Research Center (CRC) at Clinical Chemistry Pathology Laboratories, which is part of the Vanderbilt Institute for Clinical and Translational Research (VICTR), will be analyzed. The additional blood samples will be consented to and collected from healthy adult volunteers and from IBD patients as an ongoing process to add to the serum collection (FIG. 11B).

Detect DEFA5 Expression in Formalin-Fixed, Paraffin-Embedded (FFPE) IBD Biopsies/Tissues by IHC.

205 FFPE blocks were collected from IBD patients during a prior R21 funding period. Of these samples, 83 are from UC, 75 are from CC, and 47 are from IC patients. Tissues from DV patients will be used as non-IBD controls. The thin FFPE sections from these samples will be stained with anti-DEFA5 antibody at the Translational Pathology Shared Resource (TPSR). Following IHC staining, the slides will be digitally scanned using the Ariol SL-50 digital high resolution imaging system (Leica) and quantified using the Tissue IA software at the Digital Histology Shared Resource (DHSR) at Vanderbilt University. This will enable the scoring for each slide based on its staining intensity and percentage of stained cells. This digital analysis of IHC results will serve as either an additional or an alternative bioassay for DEFA5 detection in biopsies.

Determine Whether Differences in the Levels of DEFA5 in the Colonic Mucosa Tissues Correlate with Circulating Levels of DEFA5 in CC, UC or Normal Subjects.

To determine whether the level of circulating or secreted DEFA5 (sDEFA5) correlates with its level of expression in situ, biopsy samples collected from the three groups will be used to isolate mRNA to determine by real time PCR the levels of DEFA5 message present. If possible, simultaneous biopsies from areas of CC activity vs. normal, adjacent tissue will inform us regarding whether serum levels denote active disease. To that end, biopsy specimens from normal, adjacent mucosal, actively inflamed mucosa, and mucosa around the transitional zone will be examined for DEFA5 mRNA expression. A power analysis indicates that comparison of prevalence between case and control groups having 30 subjects per group would generally have 84% power to detect 40% differences (e.g. 40% vs. 80%, odds ratio 6.0) based on a two-sided test with 0.05 alpha level. In terms of precision for the prevalence estimates, when the sample size of each group is 30, a two-sided 95% confidence interval for a single proportion will be 18% from the observed rate expected to be 50%. Sample size requirements were calculated based on detecting differentially expressed proteins between two groups while controlling for the false discovery rate (FDR). The measure is the ratio of protein expression (or fold) in cases to controls for a particular protein. Effect sizes equal to 1.5 fold change with more than 80% power can be detected, based on algorithms from Jung S H, Bioinformatics 2005; 21:3097. This assumes a FDR of 0.001 and two-sided p-values, and is based on a sample of 30 cases and 30 controls. To determine the significance of sDEFA5 as a candidate biomarker of active CC and achieve a model with predictive accuracy, the models such as generalized linear model with regularization approaches and ensemble methods for feature identification including boosting, bagging, and random forest classifier will be used.

Anticipated Results, Challenges, and Alternative Procedures

It is believed that DEFA5 specific assays to detect DEFA5 in sera and tissues of IBD patients will be shown. With this, quantitative standard numerical normal reference interval (RI) values can be determined and developed for DEFA5 in sera from healthy subjects and relate these to the levels in IBD patient sera. The RI approach will be based on the central 95% of laboratory test values observed for a reference population that is free of diseases. Based on the preliminary data, it is anticipated that DEFA5 expression will be higher in tissues and sera from CC patients than in those from UC patients and that all patients with IC can be reclassified as either CC or UC patients. Although the power calculation indicated 46 patients per disease subtype, up to 100 patient tissues and sera per disease will be used from varied ethnic backgrounds to validate the detection of DEFA5 as a diagnostic tool for CC in sera.

While it is possible that the sensitivity of the assays may be poor due to relatively low levels of DEFA5 in sera, the assays will be validated by using alkaline phosphatase-conjugated anti-DEFA5 monoclonal antibodies or modify the assay to direct ELISA or a radioimmunoassay. Peroxidase-conjugated streptavidin can be used to develop a DEFA5 detection assay using 2,2'-Azinobis [3-ethylbenzothiazoline-6-sulfonic acid]-diammonium salt (ABTS) as a substrate. It is believed that the development of a sandwich assay and the antibodies will avoid cross reaction with DEFA6.

Working Example 3

Paneth cells are the differentiated progenies of the ileal epithelial stem cells (ISCs) that support the ISCs and provide antibacterial protection in mammals. Although IBD is inflammation prone, the notion that UC and CC are histologically different and require distinct surgical treatment options suggests that DEFA5 and/or specific pro-inflammatory cytokines play a major role in the pathogenesis of these diseases. It is believed that the high levels of DEFA5 in CC colectomy samples arise from aberrant metaplastic colonic crypt PCs; and that sera from patients with UC and CC contain high levels of IBD subtype specific pro-inflammatory cytokines. There is ample evidence supporting the possibility that bacterial enterotoxins such as Staphylococcal enterotoxin C and cholera toxin (Xiao-Chen Wan et al., 2008, Androutsellis-Theotokis A et al., 2011), and that pro-inflammatory cytokines such as TNF-α, IL-1β, and IFN-γ (Valdez I A et al., 2016) promote the differentiation of stem cells. However, whether bacterial enterotoxins or pro-inflammatory cytokines with or without and DEFA5 underlie the distinct pathologic features of CC relative to UC remain poorly understood. It is believed that DEFA5, bacterial enterotoxins and/or certain CC-associated pro-inflammatory cytokines promote the differentiation/expansion of colonic stem cells, and the distinct pathology associated with CC. To test this hypothesis, and in the absence of de facto animal models for CC, two different normal human colonic epithelial cell lines (NCM460 and NCM356), colonoids and/or enteroids from endoscopy biopsy tissues will be used to a) test the effects of purified DEFA5, DEFA6, and DEFA1 in the presence or absence of bacterial enterotoxins on the formation of metaplastic colonic PCs; b) assess the effects of CC- and UC-specific cytokines on DEFA5 secretion, the generation of ROS and cell viability. It is believed that DEFA5 and, to a lesser extent, DEFA6 will promote the secretion of CC-specific cytokines and the production of ROS, but attenuate both cell viability and tissue damage. It is also believed that the CC-specific cytokines will promote the synthesis/secretion of DEFA5 while the UC-specific cytokines will have the opposite effects.

Figure 8:
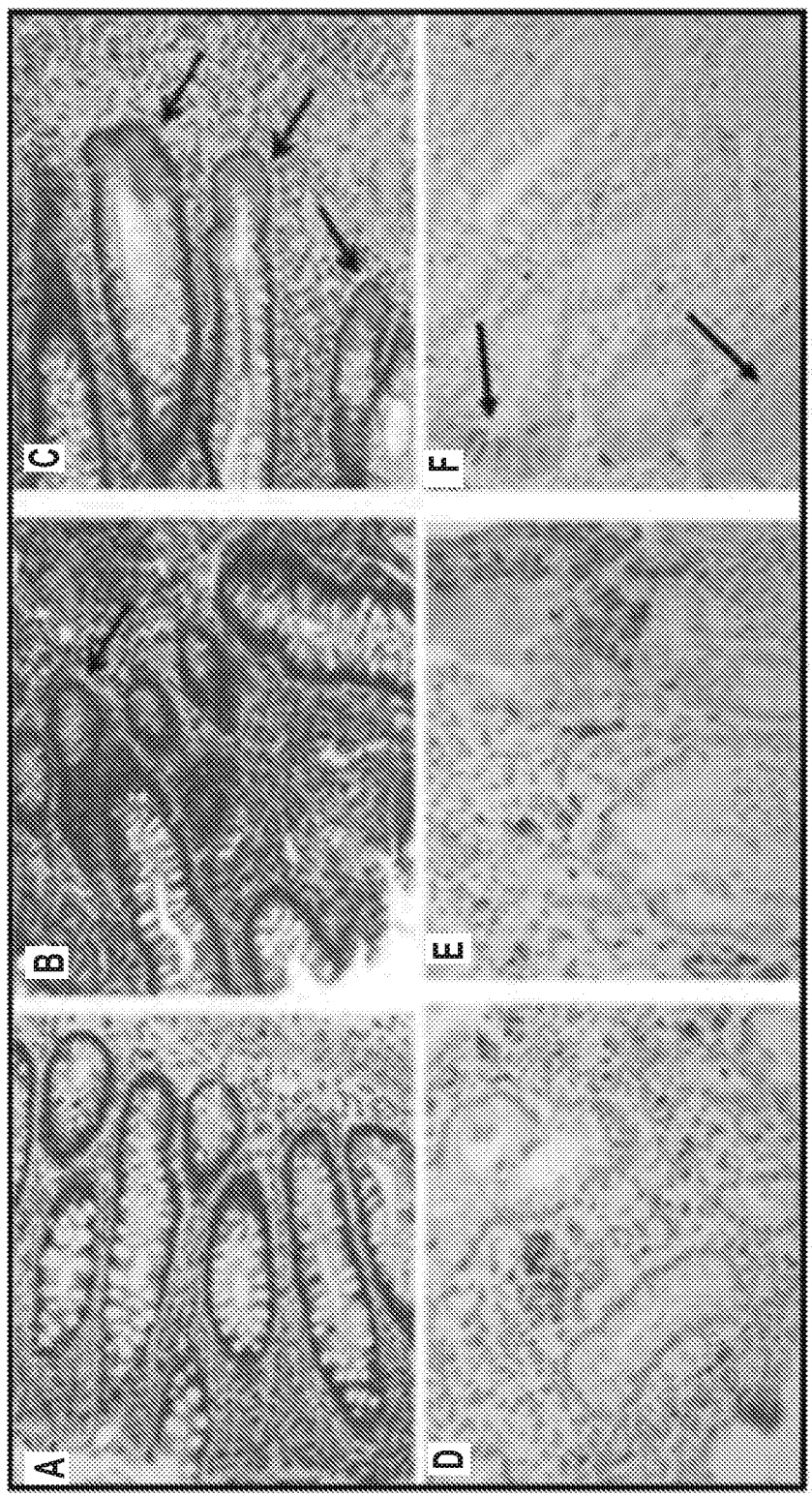
FIGS. 8A-8F illustrate representative H&E staining of colonic resected tissues.

Aberrantly expressed DEFA5 in CC patients is synthesized by metaplastic colonic crypt PCs. DEFA5 is predominantly synthesized by PCs. Therefore, it was determined whether PCs were present in the colon crypt of CC patients and to validate whether the pool of DEFA5 found in CC and in de novo CD colectomy samples originated from colonic epithelial crypts. All 20 UC samples from RPC-operated patients with de novo CD showed pools of colonic metaplastic crypt PCs, as demonstrated by H&E staining (FIGS. 8A-8C). IHC staining of lysozymes in PCs confirmed the abundance of PCs in CC colonic crypts than those in UC (FIGS. 8D-8F, arrows). FIGS. 8A-8C illustrate Representative H&E staining of colonic resected tissues. 8A, Normal colon (NLC). 8B, UC, sporadic PC (arrow). 8C, CC, with mature PCs in the crypts, (arrows). FIGS. 8D-8F illustrate representative IHC detection of DEFA5 and lysozyme in the colon. 8D, NLC. 8E, UC, (sporadic prodromal PC in one patient). 8F, CC. Magnification was at 40×.

It was found that the PCs were the DEFA5 secreting cells by staining the colectomy tissue samples for DEFA5 and lysozyme (LYZ) to detect PCs. It was found that abundant crypt PCs were present in CC samples (FIGS. 6A & 6D). Normal ileal tissues were used as control (FIG. 6G). FIGS. 6A-6I illustrate that DEFA5 and lysozyme are co-expressed in crypt PCs in CC. Double staining of de novo Crohn's tissues from two patients (6A and 6D), and normal ileum (control) (6G) with lysozyme (6B, 6E & 6F) and with DEFA5 (6C, 6F, & 6I). Merged images are shown in 6A, 6D & 6G). To ascertain that the PCs were the DEFA5 secreting cells, the colectomy tissue samples were stained for DEFA5 and lysozyme (LYZ) to detect PCs. Abundant crypt PCs were found in CC samples (FIGS. 6A & 6D). Normal ileal tissues were used as control (FIG. 6G).

Figure 9:
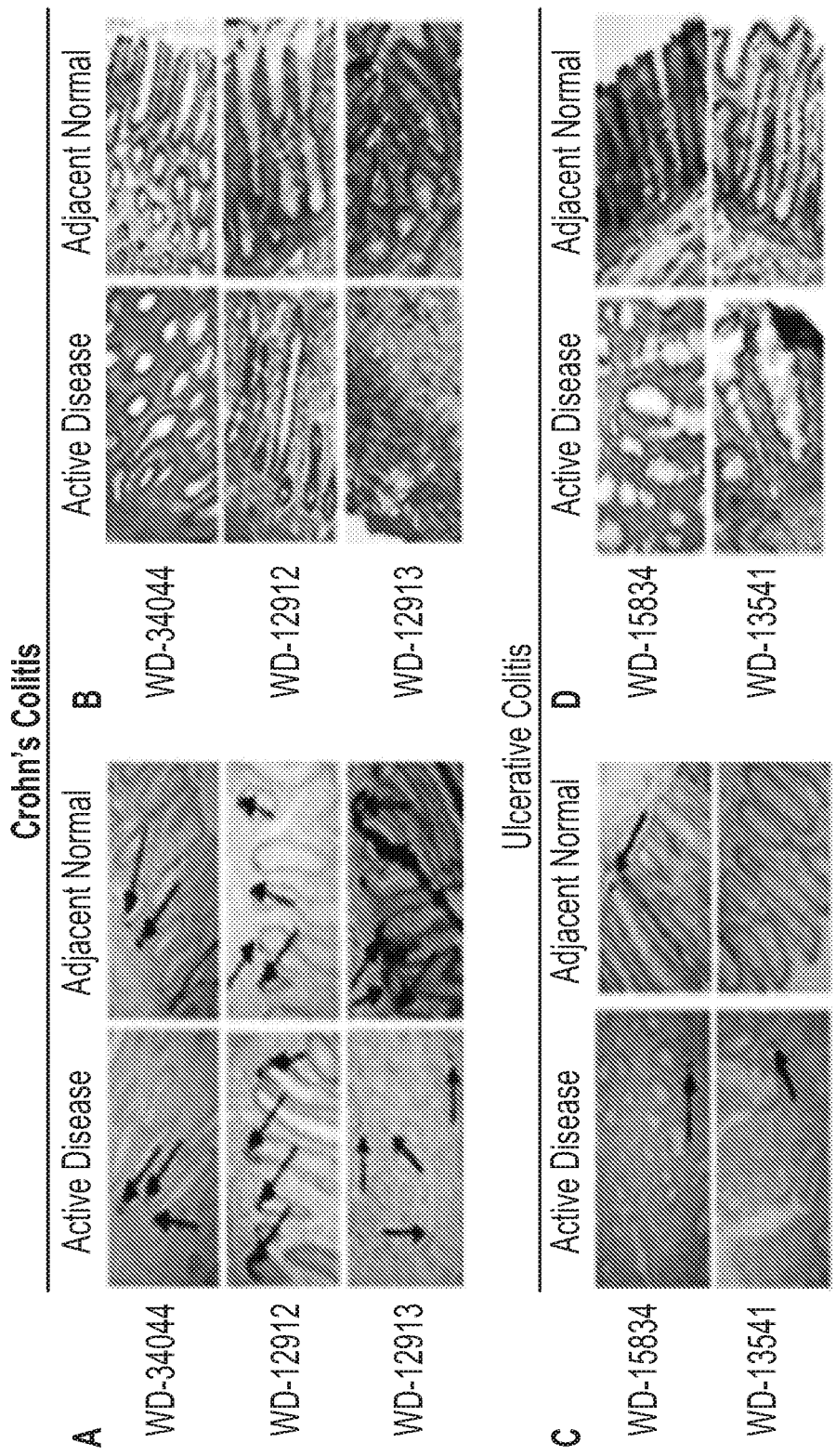
FIGS. 9A-9D illustrate IHC and H&E staining of DEFA5 in adjacent normal and diseased tissues from CC patients (A and B) and from UC patients (C and D).

FIGS. 9A-9D illustrate the presence of DEFA5 in adjacent IBD tissues. IHC and H&E staining of DEFA5 in adjacent normal and diseased tissues from CC patients (9A and 9B) and from UC patients (FIGS. 9C and 9D). Note that DEFA5 staining is not obvious in the disease and normal tissues from UC patients. DEFA5 is detected in adjacent normal tissues from CC. Given that normal healthy colon tissues lack or have scanty PCs, it was sought to determine if DEFA5 could be detected in the normal tissues adjacent to the diseased tissues in CC and UC patients. IHC for DEFA5 shows positive staining in the base of the crypts in both the inflamed and normal adjacent tissues in samples from CC patients (FIG. 9A). FIG. 9B depicts H&E. Given the co-localization of DEFA5 and PCs (FIG. 6), it is plausible to suggest that PCs are present in the diseased and normal adjacent tissues of CC patients but not in tissues from UC patients. However what triggers the appearance of PCs in this IBD disease subtype remains poorly understood.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77, or otherwise to provide organizational queues. These headings shall not limit or characterize the invention(s) set forth herein.

TABLE 2

| Gene Information | Gene Symbol | RefSeq | p-value (CC vs UC) | Fold Increase |
|---|---|---|---|---|
| NM_021010 // DEFA5 // defensin, alpha 5, Paneth cell-specific // 8p23.1 // 1670 | DEFA5 | NM_021010 | 7.23E−05 | 31.0374 |
| NM_002909 // REG1A // regenerating islet-derived 1 alpha // 2p12 // 5967 /// ENS | REG1A | NM_002909 | 0.00321456 | 21.9439 |
| NM_138938 // REG3A // regenerating islet-derived 3 alpha // 2p12 // 5068 /// NM_ | REG3A | NM_138938 | 0.000310891 | 17.3268 |
| NM_001926 // DEFA6 // defensin, alpha 6, Paneth cell-specific // 8p23.1 // 1671 | DEFA6 | NM_001926 | 0.0024893 | 16.139 |
| NM_058186 // FAM3B // family with sequence similarity 3, member B // 21q22.3 // | FAM3B | NM_058186 | 0.00116588 | 14.6887 |

TABLE 2-continued

| Gene Information | Gene Symbol | RefSeq | p-value (CC vs UC) | Fold Increase |
|---|---|---|---|---|
| NM_006507 // REG1B // regenerating islet-derived 1 beta // 2p12 // 5968 /// ENST | REG1B | NM_006507 | 0.0120953 | 13.9675 |
| NM_001074 // UGT2B7 // UDP glucuronosyltransferase 2 family, polypeptide B7 // 4 | UGT2B7 | NM_001074 | 0.0154146 | 9.92532 |
| NM_001285 // CLCA1 // chloride channel accessory 1 // 1p22.3 // 1179 /// ENST000 | CLCA1 | NM_001285 | 0.00297816 | 9.07579 |
| NM_003122 // SPINK1 // serine peptidase inhibitor, Kazal type 1 // 5q32 // 6690 | SPINK1 | NM_003122 | 0.007176 | 7.60063 |
| NM_001076 // UGT2B15 // UDP glucuronosyltransferase 2 family, polypeptide B15 // | UGT2B15 | NM_001076 | 0.0169187 | 7.12294 |
| NM_001076 // UGT2B15 // UDP glucuronosyltransferase 2 family, polypeptide B15 // | UGT2B15 | NM_001076 | 0.0169187 | 7.12294 |
| NM_000343 // SLC5A1 // solute carrier family 5 (sodium/glucose cotransporter), m | SLC5A1 | NM_000343 | 0.00447091 | 7.0494 |
| NM_000134 // FABP2 // fatty acid binding protein 2, intestinal // 4q28-q31 // 21 | FABP2 | NM_000134 | 0.0300574 | 6.63756 |
| NM_000035 // ALDOB // aldolase B, fructose-bisphosphate // 9q21.3-q22.2 // 229 / | ALDOB | NM_000035 | 0.0444145 | 6.30502 |
| NM_002770 // PRSS2 // protease, serine, 2 (trypsin 2) // 7q34 // 5645 // ENST00 | PRSS2 | NM_002770 | 0.0052665 | 6.27999 |
| NM_005379 // MYO1A // myosin IA // 12q13-q14 // 4640 /// ENST00000300119 // MYO1 | MYO1A | NM_005379 | 0.00588172 | 5.72861 |
| NM_007329 // DMBT1 // deleted in malignant brain tumors 1 // 10q26.13 // 1755 // | DMBT1 | NM_007329 | 0.0365636 | 5.56609 |
| NM_031457 // MS4A8B // membrane-spanning 4-domains, subfamily A, member 8B // 11 | MS4A8B | NM_031457 | 0.00577952 | 5.34254 |
| NM_001041 // SI // sucrase-isomaltase (alpha-glucosidase) // 3q25.2-q26.2 // 647 | SI | NM_001041 | 0.0417578 | 5.23854 |
| NM_000482 // APOA4 // apolipoprotein A-IV // 11q23 // 337 /// ENST00000357780 // | APOA4 | NM_000482 | 0.0468523 | 5.15957 |
| NM_006418 // OLFM4 // olfactomedin 4 // 13q14.3 // 10562 // ENST00000219022 // | OLFM4 | NM_006418 | 0.038931 | 5.05883 |
| NM_000482 // APOA4 // apolipoprotein A-IV // 11q23 // 337 /// ENST00000357780 // | APOA4 | NM_000482 | 0.0472178 | 4.92519 |
| NM_004133 // HNF4G // hepatocyte nuclear factor 4, gamma // 8q21.11 // 3174 /// | HNF4G | NM_004133 | 0.0113549 | 4.8964 |
| NM_017675 // CDHR2 // cadherin-related family member 2 // 5q35.2 // 54825 /// NM | CDHR2 | NM_017675 | 0.00253568 | 4.82206 |
| NM_005588 // MEP1A // meprin A, alpha (PABA peptide hydrolase) // 6p12-p11 // 42 | MEP1A | NM_005588 | 0.0198087 | 4.78504 |
| NM_002354 // EPCAM // epithelial cell adhesion molecule // 2p21 // 4072 /// ENST | EPCAM | NM_002354 | 0.0242383 | 4.77321 |
| NM_001172312 // PLS1 // plastin 1 // 3q23 // 5357 // NM_001145319 // PLS1 // pl | PLS1 | NM_001172312 | 0.0155248 | 4.73894 |
| NM_002354 // EPCAM // epithelial cell adhesion molecule // 2p21 // 4072 /// ENST | EPCAM | NM_002354 | 0.0297878 | 4.72533 |
| NM_001150 // ANPEP // alanyl (membrane) aminopeptidase // 15q25-q26 // 290 /// E | ANPEP | NM_001150 | 0.0203087 | 4.58929 |
| NM_001077 // UGT2B17 // UDP glucuronosyltransferase 2 family, polypeptide B17 // | UGT2B17 | NM_001077 | 0.0267812 | 4.51157 |
| NM_002591 // PCK1 // phosphoenolpyruvate carboxykinase 1 (soluble) // 20q13.31 / | PCK1 | NM_002591 | 0.0333639 | 4.50793 |
| NM_021804 // ACE2 // angiotensin I converting enzyme (peptidyl-dipeptidase A) 2 | ACE2 | NM_021804 | 0.0271919 | 4.49025 |
| NM_024308 // DHRS11 // dehydrogenase/reductase (SDR family) member 11 // 17q12 / | DHRS11 | NM_024308 | 0.0176773 | 4.41914 |
| NM_019010 // KRT20 // keratin 20 // 17q21.2 // 54474 /// ENST00000167588 // KRT2 | KRT20 | NM_019010 | 0.026162 | 4.35459 |
| ENST00000319509 // MUC3A // mucin 3A, cell surface associated // 7q22 // 4584 // | MUC3A | ENST00000319509 | 0.00353785 | 4.28484 |
| NM_000379 // XDH // xanthine dehydrogenase // 2p23.1 // 7498 /// ENST00000379416 | XDH | NM_000379 | 0.00289109 | 4.17476 |
| NM_007127 // VIL1 // villin 1 // 2q35 // 7429 /// ENST00000248444 // VIL1 // vil | VIL1 | NM_007127 | 0.00825691 | 4.16925 |

TABLE 2-continued

| Gene Information | Gene Symbol | RefSeq | p-value (CC vs UC) | Fold Increase |
|---|---|---|---|---|
| NM_025130 // HKDC1 // hexokinase domain containing 1 // 10q22.1 // 80201 /// ENS | HKDC1 | NM_025130 | 0.00344261 | 4.13874 |
| NR_029578 // MIR192 // microRNA 192 // 11q13.1 // 406967 | MIR192 | NR_029578 | 0.00199884 | 4.12467 |
| NM_004063 // CDH17 // cadherin 17, LI cadherin (liver-intestine) // 8q22.1 // 10 | CDH17 | NM_004063 | 0.0331015 | 4.12001 |
| NM_024922 // CES3 // carboxylesterase 3 // 16q22.1 // 23491 /// NM_001185177 // | CES3 | NM_024922 | 0.0022354 | 4.11886 |
| NM_033049 // MUC13 // mucin 13, cell surface associated // 3q21.2 // 56667 /// E | MUC13 | NM_033049 | 0.0271079 | 4.11287 |
| NM_000888 // ITGB6 // integrin, beta 6 // 2q24.2 // 3694 // ENST00000283249 // | ITGB6 | NM_000888 | 0.000602949 | 4.09738 |
| NM_004963 // GUCY2C // guanylate cyclase 2C (heat stable enterotoxin receptor) / | GUCY2C | NM_004963 | 0.00645462 | 4.0793 |
| NM_004293 // GDA // guanine deaminase // 9q21.13 // 9615 /// ENST00000358399 // | GDA | NM_004293 | 0.0208862 | 4.0739 |
| NM_001307 // CLDN7 // claudin 7 // 17p13 // 1366 /// NM_001185022 // CLDN7 // cl | CLDN7 | NM_001307 | 0.0213404 | 4.06183 |
| NR_033807 // CYP3A5 // cytochrome P450, family 3, subfamily A, polypeptide 5 // | CYP3A5 | NR_033807 | 0.0046334 | 4.04376 |
| NM_021924 // CDHR5 // cadherin-related family member 5 // 11p15.5 // 53841 /// N | CDHR5 | NM_021924 | 0.00480695 | 3.97925 |
| NM_001010922 // BCL2L15 // BCL2-like 15 // 1p13.2 // 440603 /// ENST00000393316 | BCL2L15 | NM_001010922 | 0.027053 | 3.96946 |
| NM_020770 // CGN // cingulin // 1q21 // 57530 /// ENST00000271636 // CGN // cing | CGN | NM_020770 | 0.00129584 | 3.94184 |
| NM_032787 // GPR128 // G protein-coupled receptor 128 // 3q12.2 // 84873 /// ENS | GPR128 | NM_032787 | 0.00779494 | 3.93937 |
| NM_138933 // A1CF // APOBEC1 complementation factor // 10q11.23 // 29974 /// NM_ | A1CF | NM_138933 | 0.00976589 | 3.79699 |
| NM_152311 // CLRN3 // clarin 3 // 10q26.2 // 119467 /// ENST00000368671 // CLRN3 | CLRN3 | NM_152311 | 0.0132404 | 3.74982 |
| NM_007072 // HHLA2 // HERV-H LTR-associating 2 // 3q13.13 // 11148 /// ENST00000 | HHLA2 | NM_007072 | 0.0139075 | 3.74668 |
| NM_003399 // XPNPEP2 // X-prolyl aminopeptidase (aminopeptidase P) 2, membrane-b | XPNPEP2 | NM_003399 | 0.0359348 | 3.73179 |
| NM_021258 // IL22RA1 // interleukin 22 receptor, alpha 1 // 1p36.11 // 58985 /// | IL22RA1 | NM_021258 | 0.00520995 | 3.72759 |
| NM_000149 // FUT3 // fucosyltransferase 3 (galactoside 3(4)-L-fucosyltransferase | FUT3 | NM_000149 | 0.0106419 | 3.70158 |
| NM_002644 // PIGR // polymeric immunoglobulin receptor // 1q31-q41 // 5284 /// E | PIGR | NM_002644 | 0.0363588 | 3.68869 |
| NM_001136503 // C19orf77 // chromosome 19 open reading frame 77 // 19p13.3 // 28 | C19orf77 | NM_001136503 | 0.0114867 | 3.6586 |
| NR_024626 // C17orf73 // chromosome 17 open reading frame 73 // 17q21.33 // 5501 | C17orf73 | NR_024626 | 0.00240775 | 3.64138 |
| NM_020973 // GBA3 // glucosidase, beta, acid 3 (cytosolic) // 4p15.2 // 57733 // | GBA3 | NM_020973 | 0.0362758 | 3.63402 |
| NM_023944 // CYP4F12 // cytochrome P450, family 4, subfamily F, polypeptide 12 / | CYP4F12 | NM_023944 | 0.00468827 | 3.62246 |
| NM_024320 // PRR15L // proline rich 15-like // 17q21.32 // 79170 /// ENST0000030 | PRR15L | NM_024320 | 0.0331566 | 3.60367 |
| NM_005495 // SLC17A4 // solute carrier family 17 (sodium phosphate), member 4 // | SLC17A4 | NM_005495 | 0.0299201 | 3.59753 |
| NM_001135099 // TMPRSS2 // transmembrane protease, serine 2 // 21q22.3 // 7113 / | TMPRSS2 | NM_001135099 | 0.0351257 | 3.57585 |
| NM_001193434 // C10orf81 // chromosome 10 open reading frame 81 // 10q25.3 // 79 | C10orf81 | NM_001193434 | 0.00228381 | 3.5687 |
| NM_001935 // DPP4 // dipeptidyl-peptidase 4 // 2q24.3 // 1803 /// ENST0000036053 | DPP4 | NM_001935 | 0.0302652 | 3.49144 |
| NM_001644 // APOBEC1 // apolipoprotein B mRNA editing enzyme, catalytic polypept | APOBEC1 | NM_001644 | 0.0138008 | 3.48792 |
| NM_004360 // CDH1 // cadherin 1, type 1, E-cadherin (epithelial) // 16q22.1 // 9 | CDH1 | NM_004360 | 0.010781 | 3.48059 |
| NM_024921 // POF1B // premature ovarian failure, 1B // Xq21.2 // 79983 /// ENST0 | POF1B | NM_024921 | 0.0313161 | 3.44457 |
| NM_002416 // CXCL9 // chemokine (C-X-C motif) ligand 9 // 4q21 // 4283 /// ENST0 | CXCL9 | NM_002416 | 0.00248734 | 3.44146 |
| NM_014479 // ADAMDEC1 // ADAM-like, decysin 1 // 8p21.2 // 27299 /// NM_00114527 | ADAMDEC1 | NM_014479 | 0.00203661 | 3.42469 |

TABLE 2-continued

| Gene Information | Gene Symbol | RefSeq | p-value (CC vs UC) | Fold Increase |
|---|---|---|---|---|
| NM_001112706 // SCIN // scinderin // 7p21.3 // 85477 /// NM_033128 // SCIN // sc | SCIN | NM_001112706 | 0.00493508 | 3.3952 |
| NR_024345 // NCRNA00262 // non-protein coding RNA 262 // 12q24.31 // 283460 | NCRNA00262 | NR_024345 | 0.037473 | 3.39502 |
| NM_002273 // KRT8 // keratin 8 // 12q13 // 3856 /// ENST00000293308 // KRT8 // k | KRT8 | NM_002273 | 0.0146545 | 3.39222 |
| NM_001038603 // MARVELD2 // MARVEL domain containing 2 // 5q13.2 // 153562 /// E | MARVELD2 | NM_001038603 | 0.0179974 | 3.37682 |
| NM_001038603 // MARVELD2 // MARVEL domain containing 2 // 5q13.2 // 153562 /// E | MARVELD2 | NM_001038603 | 0.0179974 | 3.37682 |
| NM_144575 // CAPN13 // calpain 13 // 2p22-p21 // 92291 /// ENST00000295055 // CA | CAPN13 | NM_144575 | 0.013239 | 3.36885 |
| NM_022129 // PBLD // phenazine biosynthesis-like protein domain containing // 10 | PBLD | NM_022129 | 0.00497915 | 3.3666 |
| NM_000775 // CYP2J2 // cytochrome P450, family 2, subfamily J, polypeptide 2 // | CYP2J2 | NM_000775 | 0.0196093 | 3.36302 |
| NM_001135195 // SLC39A5 // solute carrier family 39 (metal ion transporter), mem | SLC39A5 | NM_001135195 | 0.00623473 | 3.34227 |
| NM_138788 // TMEM45B // transmembrane protein 45B // 11q24.3 // 120224 /// ENST0 | TMEM45B | NM_138788 | 0.0306305 | 3.33725 |
| NM_176813 // AGR3 // anterior gradient homolog 3 (Xenopus laevis) // 7p21.1 // 1 | AGR3 | NM_176813 | 0.0400823 | 3.32266 |
| NM_022901 // LRRC19 // leucine rich repeat containing 19 // 9p21.2 // 64922 /// | LRRC19 | NM_022901 | 0.0294679 | 3.31296 |
| NM_139053 // EPS8L3 // EPS8-like 3 // 1p13.3 // 79574 /// NM_133181 // EPS8L3 // | EPS8L3 | NM_139053 | 0.00371579 | 3.29224 |
| NM_017697 // ESRP1 // epithelial splicing regulatory protein 1 // 8q22.1 // 5484 | ESRP1 | NM_017697 | 0.0234665 | 3.27492 |
| NM_002457 // MUC2 // mucin 2, oligomeric mucus/gel-forming // 11p15.5 // 4583 // | MUC2 | NM_002457 | 0.0182535 | 3.26416 |
| NR_001296 // TRY6 // trypsinogen C // 7q34 // 154754 /// NM_002770 // PRSS2 // p | TRY6 | NR_001296 | 0.0203767 | 3.24356 |
| NM_002773 // PRSS8 // protease, serine, 8 // 16p11.2 // 5652 // ENST00000317508 | PRSS8 | NM_002773 | 0.0131026 | 3.2405 |
| NM_025214 // CCDC68 // coiled-coil domain containing 68 // 18q21 // 80323 /// NM | CCDC68 | NM_025214 | 0.00627753 | 3.2264 |
| NM_001943 // DSG2 // desmoglein 2 // 18q12.1 // 1829 /// ENST00000261590 // DSG2 | DSG2 | NM_001943 | 0.0357587 | 3.22627 |
| NM_000772 // CYP2C18 // cytochrome P450, family 2, subfamily C, polypeptide 18 / | CYP2C18 | NM_000772 | 0.0100284 | 3.20876 |
| NM_000767 // CYP2B6 // cytochrome P450, family 2, subfamily B, polypeptide 6 // | CYP2B6 | NM_000767 | 0.00589423 | 3.19484 |
| NM_016234 // ACSL5 // acyl-CoA synthetase long-chain family member 5 // 10q25.1- | ACSL5 | NM_016234 | 0.00353915 | 3.19242 |
| NM_145865 // ANKS4B // ankyrin repeat and sterile alpha motif domain containing | ANKS4B | NM_145865 | 0.027168 | 3.16823 |
| NM_032579 // RETNLB // resistin like beta // 3q13.1 // 84666 /// ENST00000295755 | RETNLB | NM_032579 | 0.0226491 | 3.14305 |
| NM_021978 // ST14 // suppression of tumorigenicity 14 (colon carcinoma) // 11q24 | ST14 | NM_021978 | 0.0143682 | 3.14171 |
| NM_000492 // CFTR // cystic fibrosis transmembrane conductance regulator (ATP-bi | CFTR | NM_000492 | 0.0330127 | 3.13524 |
| NM_018842 // BAIAP2L1 // BAI1-associated protein 2-like 1 // 7q22.1 // 55971 /// | BAIAP2L1 | NM_018842 | 0.00626097 | 3.13099 |
| NM_001165958 // GSDMB // gasdermin B // 17q12 // 55876 /// NM_001042471 // GSDMB | GSDMB | NM_001165958 | 0.0013942 | 3.1309 |
| NM_024422 // DSC2 // desmocollin 2 // 18q12.1 // 1824 /// NM_004949 // DSC2 // d | DSC2 | NM_024422 | 0.0115939 | 3.11862 |
| NM_006017 // PROM1 // prominin 1 // 4p15.32 // 8842 /// NM_001145847 // PROM1 // | PROM1 | NM_006017 | 0.0116042 | 3.10273 |
| NM_017878 // HRASLS2 // HRAS-like suppressor 2 // 11q12.3 // 54979 /// ENST00000 | HRASLS2 | NM_017878 | 0.0267887 | 3.09847 |
| NM_002203 // ITGA2 // integrin, alpha 2 (CD49B, alpha 2 subunit of VLA-2 recepto | ITGA2 | NM_002203 | 0.00793505 | 3.07141 |
| NM_005123 // NR1H4 // nuclear receptor subfamily 1, group H, member 4 // 12q23.1 | NR1H4 | NM_005123 | 0.0456782 | 3.06865 |
| NM_001145862 // MTMR11 // myotubularin related protein 11 // 1q12-q21 // 10903 / | MTMR11 | NM_001145862 | 0.00116554 | 3.03455 |

TABLE 2-continued

| Gene Information | Gene Symbol | RefSeq | p-value (CC vs UC) | Fold Increase |
|---|---|---|---|---|
| NM_018414 // ST6GALNAC1 // ST6 (alpha-N-acetyl-neuraminyl-2,3-beta-galactosyl-1, | ST6GALNAC1 | NM_018414 | 0.0240185 | 3.0202 |
| NM_001080527 // MYO7B // myosin VIIB // 2q21.1 // 4648 // ENST00000428314 // MY | MYO7B | NM_001080527 | 0.00130692 | 2.99927 |
| NM_002153 // HSD17B2 // hydroxysteroid (17-beta) dehydrogenase 2 // 16q24.1-q24. | HSD17B2 | NM_002153 | 0.0213389 | 2.99803 |
| AK095678 // LOC151009 // hypothetical LOC151009 // 2q13 // 151009 /// AK056084 / | LOC151009 | AK095678 | 0.000466288 | 2.99502 |
| NM_000769 // CYP2C19 // cytochrome P450, family 2, subfamily C, polypeptide 19 / | CYP2C19 | NM_000769 | 0.0193957 | 2.99186 |
| NM_000790 // DDC // dopa decarboxylase (aromatic L-amino acid decarboxylase) // | DDC | NM_000790 | 0.0257511 | 2.98778 |
| NM_001143948 // C6orf105 // chromosome 6 open reading frame 105 // 6p24.1 // 848 | C6orf105 | NM_001143948 | 0.0220945 | 2.95786 |
| NM_001015001 // CKMT1A // creatine kinase, mitochondrial 1A // 15q15 / 548596 / | CKMT1A | NM_001015001 | 0.042629 | 2.95709 |
| NM_001015001 // CKMT1A // creatine kinase, mitochondrial 1A // 15q15 // 548596 / | CKMT1A | NM_001015001 | 0.042629 | 2.95709 |
| NM_019893 // ASAH2 // N-acylsphingosine amidohydrolase (non-lysosomal ceramidase | ASAH2 | NM_019893 | 0.0167497 | 2.95643 |
| NM_001002236 // SERPINA1 // serpin peptidase inhibitor, clade A (alpha-1 antipro | SERPINA1 | NM_001002236 | 0.0170929 | 2.94245 |
| NM_002031 // FRK // fyn-related kinase // 6q21-q22.3 // 2444 /// ENST0000368626 | FRK | NM_002031 | 0.0177896 | 2.93608 |
| NM_001190482 // PCSK5 // proprotein convertase subtilisin/kexin type 5 // 9q21.3 | PCSK5 | NM_001190482 | 0.00160967 | 2.92603 |
| NM_004415 // DSP // desmoplakin // 6p24 // 1832 /// NM_001008844 // DSP // desmo | DSP | NM_004415 | 0.0116502 | 2.91732 |
| NM_004591 // CCL20 // chemokine (C-C motif) ligand 20 // 2q33-q37 // 6364 /// NM | CCL20 | NM_004591 | 0.0229351 | 2.91511 |
| NM_000561 // GSTM1 // glutathione S-transferase mu 1 // 1p13.3 // 2944 /// NM_14 | GSTM1 | NM_000561 | 0.032505 | 2.91233 |
| NM_000927 // ABCB1 // ATP-binding cassette, sub-family B (MDR/TAP), member 1 // | ABCB1 | NM_000927 | 0.03279 | 2.89709 |
| NM_000187 // HGD // homogentisate 1,2-dioxygenase // 3q13.33 // 3081 /// ENST000 | HGD | NM_000187 | 0.0180393 | 2.8961 |
| NM_000187 / HGD // homogentisate 1,2-dioxygenase // 3q13.33 // 3081 /// ENST000 | HGD | NM_000187 | 0.0180393 | 2.8961 |
| NM_153676 // USH1C // Usher syndrome 1C (autosomal recessive, severe) // 11p14.3 | USH1C | NM_153676 | 0.00547469 | 2.88241 |
| NM_005624 // CCL25 // chemokine (C-C motif) ligand 25 // 19p13.2 // 6370 // ENS | CCL25 | NM_005624 | 0.0492359 | 2.86049 |
| NM_004174 // SLC9A3 // solute carrier family 9 (sodium/hydrogen exchanger), memb | SLC9A3 | NM_004174 | 0.0173616 | 2.8567 |
| NM_001306 // CLDN3 // claudin 3 // 7q11.23 // 1365 /// ENST00000395145 // CLDN3 | CLDN3 | NM_001306 | 0.0490185 | 2.84657 |
| NM_001114309 // ELF3 // E74-like factor 3 (ets domain transcription factor, epit | ELF3 | NM_001114309 | 0.00265363 | 2.84098 |
| NM_000507 // FBP1 // fructose-1,6-bisphosphatase 1 // 9q22.3 // 2203 /// NM_0011 | FBP1 | NM_000507 | 0.022351 | 2.83767 |
| NM_025257 // SLC44A4 // solute carrier family 44, member 4 // 6p21.3 // 80736 // | SLC44A4 | NM_025257 | 0.0415598 | 2.83697 |
| NM_025257 // SLC44A4 // solute carrier family 44, member 4 // 6p21.3 // 80736 // | SLC44A4 | NM_025257 | 0.0415598 | 2.83697 |
| NM_025257 // SLC44A4 // solute carrier family 44, member 4 // 6p21.3 // 80736 // | SLC44A4 | NM_025257 | 0.0415598 | 2.83697 |
| NM_001017970 // TMEM30B // transmembrane protein 30B // 14q23.1 // 161291 /// EN | TMEM30B | NM_001017970 | 0.00717685 | 2.83259 |
| NM_003963 // TM4SF5 // transmembrane 4 L six family member 5 // 17p13.3 // 9032 | TM4SF5 | NM_003963 | 0.0295851 | 2.82875 |
| NM_002242 // KCNJ13 // potassium inwardly-rectifying channel, subfamily J, membe | KCNJ13 | NM_002242 | 0.0400838 | 2.82471 |
| NM_017655 // GIPC2 // GIPC PDZ domain containing family, member 2 // 1p31.1 // 5 | GIPC2 | NM_017655 | 0.0155498 | 2.81938 |
| NM_001127605 // LIPA // lipase A, lysosomal acid, cholesterol esterase // 10q23. | LIPA | NM_001127605 | 0.000449938 | 2.81611 |
| NM_001249 // ENTPD5 // ectonucleoside triphosphate diphosphohydrolase 5 // 14q24 | ENTPD5 | NM_001249 | 0.0118697 | 2.81265 |

TABLE 2-continued

| Gene Information | Gene Symbol | RefSeq | p-value (CC vs UC) | Fold Increase |
|---|---|---|---|---|
| NM_005358 // LMO7 // LIM domain 7 // 13q22.2 // 4008 /// NM_015842 // LMO7 // LI | LMO7 | NM_005358 | 0.00460576 | 2.80795 |
| NM_018667 // SMPD3 // sphingomyelin phosphodiesterase 3, neutral membrane (neutr | SMPD3 | NM_018667 | 0.00228114 | 2.80665 |
| NM_004563 // PCK2 // phosphoenolpyruvate carboxykinase 2 (mitochondrial) // 14q1 | PCK2 | NM_004563 | 0.00983672 | 2.79262 |
| NM_003657 // BCAS1 // breast carcinoma amplified sequence 1 // 20q13.2 // 8537 / | BCAS1 | NM_003657 | 0.0213345 | 2.78368 |
| NM_024850 // BTNL8 // butyrophilin-like 8 // 5q35.3 // 79908 /// NM_001040462 // | BTNL8 | NM_024850 | 0.0446038 | 2.7769 |
| NM_020672 // S100A14 // S100 calcium binding protein A14 // 1q21.3 // 57402 / | S100A14 | NM_020672 | 0.0202797 | 2.77156 |
| NM_033229 // TRIM15 // tripartite motif-containing 15 // 6p21.3 // 89870 /// ENS | TRIM15 | NM_033229 | 0.0097609 | 2.77095 |
| NM_033229 // TRIM15 // tripartite motif-containing 15 // 6p21.3 // 89870 /// ENS | TRIM15 | NM_033229 | 0.0097609 | 2.77095 |
| NM_033229 // TRIM15 // tripartite motif-containing 15 // 6p21.3 // 89870 /// ENS | TRIM15 | NM_033229 | 0.0097609 | 2.77095 |
| NM_001144060 // NHSL1 // NHS-like 1 // 6q23.3 // 57224 // NM_020464 // NHSL1 // | NHSL1 | NM_001144060 | 0.0124428 | 2.7705 |
| NM_003869 // CES2 // carboxylesterase 2 // 16q22.1 // 8824 /// NR_036684 // CES2 | CES2 | NM_003869 | 0.0197746 | 2.76326 |
| NM_199187 // KRT 18 // keratin 18 // 12q13 // 3875 /// NM_000224 // KRT18 // kera | KRT18 | NM_199187 | 0.0272938 | 2.7567 |
| NM_002842 // PTPRH // protein tyrosine phosphatase, receptor type, H // 19q13.4 | PTPRH | NM_002842 | 0.00126103 | 2.75623 |
| NM_001105248 // TMC5 // transmembrane channel-like 5 // 16p12.3 // 79838 /// NM | TMC5 | NM_001105248 | 0.015439 | 2.74553 |
| NM_001145809 // MYH14 // myosin, heavy chain 14, non-muscle // 19q13.33 // 79784 | MYH14 | NM_001145809 | 0.00203315 | 2.74198 |
| NM_001054 // SULT1A2 // sulfotransferase family, cytosolic, 1A, phenol-preferrin | SULT1A2 | NM_001054 | 0.0273843 | 2.73 |
| NM_024850 // BTNL8 // butyrophilin-like 8 // 5q35.3 // 79908 /// NM_001159708 // | BTNL8 | NM_024850 | 0.0433332 | 2.7165 |
| NM_006147 // IRF6 // interferon regulatory factor 6 // 1q32.3-q41 // 3664 /// EN | IRF6 | NM_006147 | 0.00663477 | 2.71435 |
| NM_000457 // HNF4A // hepatocyte nuclear factor 4, alpha // 20q13.12 // 3172 /// | HNF4A | NM_000457 | 0.00414138 | 2.70616 |
| NM_138809 // CMBL // carboxymethylenebutenolidase homolog (Pseudomonas) // 5p15. | CMBL | NM_138809 | 0.0336993 | 2.69623 |
| NM_001080467 // MYO5B / myosin VB // 18q21 // 4645 /// ENST00000285039 // MYO5B | MYO5B | NM_001080467 | 0.00639465 | 2.69568 |
| NM_153274 // BEST4 // bestrophin 4 // 1p33-p32.3 // 266675 /// ENST00000372207 / | BEST4 | NM_153274 | 0.0313639 | 2.68747 |
| NM_020775 // KIAA1324 // KIAA1324 // 1p13.3 // 57535 /// ENST00000234923 // KIAA | KIAA1324 | NM_020775 | 0.0214297 | 2.68133 |
| NM_001004320 // TMEM195 // transmembrane protein 195 // 7p21.2 // 392636 /// ENS | TMEM195 | NM_001004320 | 0.0149666 | 2.67293 |
| NM_001091 // ABP1 // amiloride binding protein 1 (amine oxidase (copper-containi | ABP1 | NM_001091 | 0.0487109 | 2.66772 |
| NM_016245 // HSD17B11 // hydroxysteroid (17-beta) dehydrogenase 11 // 4q22.1 // | HSD17B11 | NM_016245 | 0.0216559 | 2.66473 |
| NM_006144 // GZMA // granzyme A (granzyme 1, cytotoxic T-lymphocyte-associated s | GZMA | NM_006144 | 0.00618242 | 2.66284 |
| NM_001039372 // HEPACAM2 // HEPACAM family member 2 // 7q21.3 // 253012 // NM_1 | HEPACAM2 | NM_001039372 | 0.0201907 | 2.6524 |
| NM_001197097 // PRSS3 // protease, serine, 3 // 9p11.2 // 5646 /// NM_007343 // | PRSS3 | NM_001197097 | 0.0173103 | 2.63924 |
| NM_012214 // MGAT4A // mannosyl (alpha-1,3-)-glycoprotein beta-1,4-N-acetylgluco | MGAT4A | NM_012214 | 0.00113208 | 2.62742 |
| NM_019894 // TMPRSS4 // transmembrane protease, serine 4 // 11q23.3 // 56649 /// | TMPRSS4 | NM_019894 | 0.0362683 | 2.60764 |
| NM_003810 // TNFSF10 // tumor necrosis factor (ligand) superfamily, member 10 // | TNFSF10 | NM_003810 | 0.0129809 | 2.60509 |
| NM_022842 // CDCP1 // CUB domain containing protein 1 // 3p21.31 // 64866 /// NM | CDCP1 | NM_022842 | 0.0167874 | 2.60268 |

TABLE 2-continued

| Gene Information | Gene Symbol | RefSeq | p-value (CC vs UC) | Fold Increase |
|---|---|---|---|---|
| NM_001136493 // MFSD2A // major facilitator superfamily domain containing 2A // | MFSD2A | NM_001136493 | 0.00343618 | 2.59815 |
| NM_018265 // C1orf106 // chromosome 1 open reading frame 106 // 1q32.1 // 55765 | C1orf106 | NM_018265 | 0.00613223 | 2.59677 |
| NM_000063 // C2 // complement component 2 // 6p21.3 // 717 /// NM_001145903 // C | C2 | NM_000063 | 0.0117239 | 2.59406 |
| NM_000063 // C2 // complement component 2 // 6p21.3 // 717 /// NM_001145903 / C | C2 | NM_000063 | 0.0117239 | 2.59406 |
| NM_000625 // NOS2 // nitric oxide synthase 2, inducible // 17q11.2-q12 // 4843 / | NOS2 | NM_000625 | 0.0089305 | 2.59304 |
| NM_001677 // ATP1B1 // ATPase, Na+/K+ transporting, beta 1 polypeptide // 1q24 // | ATP1B1 | NM_001677 | 0.0131783 | 2.58871 |
| NM_004751 // GCNT3 // glucosaminyl (N-acetyl) transferase 3, mucin type // 15q21 | GCNT3 | NM_004751 | 0.0432197 | 2.58761 |
| NM_002021 // FMO1 // flavin containing monooxygenase 1 // 1q24.3 // 2326 // ENS | FMO1 | NM_002021 | 0.0408097 | 2.57646 |
| NM_033292 // CASP1 // caspase 1, apoptosis-related cysteine peptidase (interleuk | CASP1 | NM_033292 | 0.00634065 | 2.57013 |
| NM_147161 // ACOT11 // acyl-CoA thioesterase 11 // 1p32.3 // 26027 /// ENST00000 | ACOT11 | NM_147161 | 0.0462671 | 2.53682 |
| NM_001039112 // FER1L6 // fer-1-like 6 (C. elegans) // 8924.1 // 654463 /// ENST | FER1L6 | NM_001039112 | 0.0413201 | 2.53444 |
| NM_212543 // B4GALT4 // UDP-Gal:betaGlcNAc beta 1,4-galactosyltransferase, poly | B4GALT4 | NM_212543 | 0.00083206 | 2.53146 |
| NM_182762 // MACC1 // metastasis associated in colon cancer 1 // 7p21.1 // 34638 | MACC1 | NM_182762 | 0.0113734 | 2.52994 |
| NM_001461 // FMO5 // flavin containing monooxygenase 5 // 1q21.1 // 2330 /// NM | FMO5 | NM_001461 | 0.0227505 | 2.52925 |
| NM_031219 // HDHD3 // haloacid dehalogenase-like hydrolase domain containing 3 / | HDHD3 | NM_031219 | 0.00048055 | 2.52696 |
| NM_001010872 // FAM83B // family with sequence similarity 83, member B // 6p12.1 | FAM83B | NM_001010872 | 0.00806204 | 2.52496 |
| NM_024533 // CHST5 // carbohydrate (N-acetylglucosamine 6-O) sulfotransferase 5 | CHST5 | NM_024533 | 0.026327 | 2.51739 |
| NM_000063 // C2 // complement component 2 // 6p21.3 // 717 /// NM_001145903 // C | C2 | NM_000063 | 0.0114041 | 2.51419 |
| NM_004624 // VIPR1 // vasoactive intestinal peptide receptor 1 // 3p22 // 7433 / | VIPR1 | NM_004624 | 0.00331244 | 2.50863 |
| NM_004572 // PKP2 // plakophilin 2 // 12p11 // 5318 /// NM_001005242 // PKP2 // | PKP2 | NM_004572 | 0.042448 | 2.49612 |
| NM_032521 // PARD6B // par-6 partitioning defective 6 homolog beta (C. elegans) | PARD6B | NM_032521 | 0.00395798 | 2.49598 |
| NM_024915 // GRHL2 // grainyhead-like 2 (Drosophila) // 8q22.3 // 79977 /// ENST | GRHL2 | NM_024915 | 0.00624177 | 2.49455 |
| NM_003982 // SLC7A7 // solute carrier family 7 (cationic amino acid transporter, | SLC7A7 | NM_003982 | 0.00813405 | 2.49274 |
| NM_198584 // CA13 // carbonic anhydrase XIII // 8q21.2 // 377677 /// ENST0000032 | CA13 | NM_198584 | 0.00510852 | 2.48988 |
| ENST00000319509 // MUC3A // mucin 3A, cell surface associated // 7q22 // 4584 // | MUC3A | ENST00000319509 | 0.0135883 | 2.4817 |
| NM_021102 // SPINT2 // serine peptidase inhibitor, Kunitz type, 2 // 19q13.1 // | SPINT2 | NM_021102 | 0.0219176 | 2.48131 |
| NM_080489 // SDCBP2 // syndecan binding protein (syntenin) 2 // 20p13 // 27111 / | SDCBP2 | NM_080489 | 0.000789754 | 2.47862 |
| NM_001144967 // NEDD4L // neural precursor cell expressed, developmentally down- | NEDD4L | NM_001144967 | 0.0227827 | 2.47791 |
| NM_001982 // ERBB3 // v-erb-b2 erythroblastic leukemia viral oncogene homolog 3 | ERBB3 | NM_001982 | 0.0175723 | 2.47531 |
| NM_000240 // MAOA // monoamine oxidase A // Xp11.3 // 4128 /// ENST00000338702 / | MAOA | NM_000240 | 0.0446884 | 2.47082 |
| NM_182960 // PRELID2 // PRELI domain containing 2 // 5q32 // 153768 /// NM_13849 | PRELID2 | NM_182960 | 0.00837834 | 2.47032 |
| NM_017720 // STAP2 // signal transducing adaptor family member 2 // 19p13.3 // 5 | STAP2 | NM_017720 | 0.016285 | 2.46781 |
| NM_138700 // TRIM40 // tripartite motif-containing 40 // 6p22.1 // 135644 /// EN | TRIM40 | NM_138700 | 0.0336507 | 2.45989 |
| NM_000050 // ASS1 // argininosuccinate synthase 1 // 9q34.1 // 445 /// NM_054012 | ASS1 | NM_000050 | 0.0132614 | 2.43678 |

TABLE 2-continued

| Gene Information | Gene Symbol | RefSeq | p-value (CC vs UC) | Fold Increase |
|---|---|---|---|---|
| NM_005021 // ENPP3 // ectonucleotide pyrophosphatase/phosphodiesterase 3 // 6q22 | ENPP3 | NM_005021 | 0.0149678 | 2.43651 |
| NM_001130080 // IFI27 // interferon, alpha-inducible protein 27 // 14q32 // 3429 | IFI27 | NM_001130080 | 0.0140236 | 2.43613 |
| NM_001979 // EPHX2 // epoxide hydrolase 2, cytoplasmic // 8p21 // 2053 /// BC011 | EPHX2 | NM_001979 | 0.00690804 | 2.43531 |
| NM_017700 // ARHGEF38 // Rho guanine nucleotide exchange factor (GEF) 38 // 4q24 | ARHGEF38 | NM_017700 | 0.00476968 | 2.42966 |
| NM_019080 // NDFIP2 // Nedd4 family interacting protein 2 // 13q31.1 // 54602 // | NDFIP2 | NM_019080 | 0.00576011 | 2.42832 |
| NM_001135181 // SLC5A9 // solute carrier family 5 (sodium/glucose cotransporter) | SLC5A9 | NM_001135181 | 0.0296431 | 2.42215 |
| NM_032717 // AGPAT9 // 1-acylglycerol-3-phosphate O-acyltransferase 9 // 4q21.23 | AGPAT9 | NM_032717 | 0.0147877 | 2.41843 |
| NM_001145303 // TMC4 // transmembrane channel-like 4 // 19q13.42 // 147798 /// N | TMC4 | NM_001145303 | 0.00110774 | 2.41442 |
| NM_138700 // TRIM40 // tripartite motif-containing 40 // 6p22.1 // 135644 /// EN | TRIM40 | NM_138700 | 0.0250665 | 2.41358 |
| NM_138700 // TRIM40 // tripartite motif-containing 40 // 6p22.1 // 135644 /// EN | TRIM40 | NM_138700 | 0.0250665 | 2.41358 |
| NM_203463 // LASS6 // LAG1 homolog, ceramide synthase 6 // 2q24.3 // 253782 /// | LASS6 | NM_203463 | 0.00156196 | 2.41203 |
| NM_001730 // KLF5 // Kruppel-like factor 5 (intestinal) // 13q22.1 // 688 /// EN | KLF5 | NM_001730 | 0.0129015 | 2.40278 |
| NM_001265 // CDX2 // caudal type homeobox 2 // 13q12.3 // 1045 /// ENST000003810 | CDX2 | NM_001265 | 0.0471437 | 2.402 |
| NM_000239 // LYZ // lysozyme // 12q15 // 4069 /// ENST00000261267 // LYZ // lyso | LYZ | NM_000239 | 0.0118582 | 2.39899 |
| NM_022772 // EPS8L2 // EPS8-like 2 // 11p15.5 // 64787 /// ENST00000318562 // EP | EPS8L2 | NM_022772 | 0.00191717 | 2.39231 |
| NM_025153 // ATP10B // ATPase, class V, type 10B // 5q34 // 23120 /// ENST000003 | ATP10B | NM_025153 | 0.0273664 | 2.38677 |
| NM_178445 // CCRL1 // chemokine (C-C motif) receptor-like 1 // 3q22 // 51554 /// | CCRL1 | NM_178445 | 0.0328488 | 2.38032 |
| NM_001031803 // LLGL2 // lethal giant larvae homolog 2 (Drosophila) // 17q25.1 / | LLGL2 | NM_001031803 | 0.00351395 | 2.36948 |
| NM_175058 // PLEKHA7 // pleckstrin homology domain containing, family A member 7 | PLEKHA7 | NM_175058 | 0.00170237 | 2.36502 |
| NM_006714 // SMPDL3A // sphingomyelin phosphodiesterase, acid-like 3A // 6q22.31 | SMPDL3A | NM_006714 | 0.0236138 | 2.36218 |
| NR_024158 // LOC25845 // hypothetical LOC25845 // 5p15.33 // 25845 /// ENST00000 | LOC25845 | NR_024158 | 0.0297858 | 2.35341 |
| NM_016339 // RAPGEFL1 // Rap guanine nucleotide exchange factor (GEF)-like 1 // | RAPGEFL1 | NM_016339 | 0.026897 | 2.3526 |
| NM_015888 // HOOK1 // hook homolog 1 (Drosophila) // 1p32.1 // 51361 /// ENST000 | HOOK1 | NM_015888 | 0.0336071 | 2.34842 |
| NM_138737 // HEPH // hephaestin // Xq11-q12 // 9843 /// NM_001130860 // HEPH // | HEPH | NM_138737 | 0.0118198 | 2.34595 |
| NM_012079 // DGAT1 // diacylglycerol O-acyltransferase 1 // 8q24.3 // 8694 /// E | DGAT1 | NM_012079 | 0.023252 | 2.34522 |
| NM_012079 // DGAT1 // diacylglycerol O-acyltransferase 1 // 8q24.3 // 8694 /// E | DGAT1 | NM_012079 | 0.023252 | 2.34522 |
| NM_001017535 // VDR // vitamin D (1,25-dihydroxyvitamin D3) receptor // 12q13.1 | VDR | NM_001017535 | 0.0115491 | 2.34153 |
| NM_001029874 // REP15 // RAB 15 effector protein // 12p11.22 // 387849 /// ENST00 | REP15 | NM_001029874 | 0.0477963 | 2.33656 |
| NM_198495 // CTAGE4 // CTAGE family, member 4 // 7q35 // 100128553 /// NM_001145 | CTAGE4 | NM_198495 | 0.00065154 | 2.33596 |
| NM_006548 // IGF2BP2 // insulin-like growth factor 2 mRNA binding protein 2 // 3 | IGF2BP2 | NM_006548 | 8.80E−05 | 2.33476 |
| NM_002985 // CCL5 // chemokine (C-C motif) ligand 5 // 17q11.2-q12 // 6352 /// E | CCL5 | NM_002985 | 0.0247261 | 2.33002 |
| NM_001005328 // OR2A7 // olfactory receptor, family 2, subfamily A, member 7 // | OR2A7 | NM_001005328 | 0.00337105 | 2.32021 |
| NM_018284 // GBP3 // guanylate binding protein 3 // 1p22.2 // 2635 /// ENST00000 | GBP3 | NM_018284 | 0.013933 | 2.31798 |
| NM_002829 // PTPN3 // protein tyrosine phosphatase, non-receptor type 3 // 9q31 | PTPN3 | NM_002829 | 0.0212048 | 2.31511 |
| NM_021073 // BMP5 // bone morphogenetic protein 5 // 6p12.1 // 653 /// ENST00000 | BMP5 | NM_021073 | 0.0201876 | 2.31001 |

TABLE 2-continued

| Gene Information | Gene Symbol | RefSeq | p-value (CC vs UC) | Fold Increase |
|---|---|---|---|---|
| NM_178176 // MOGAT3 // monoacylglycerol O-acyltransferase 3 // 7q22.1 // 346606 | MOGAT3 | NM_178176 | 0.00641018 | 2.30988 |
| NM_000666 // ACY1 // aminoacylase 1 // 3p21.1 // 95 /// L07548 // ACY1 // aminoa | ACY1 | NM_000666 | 0.0261486 | 2.30581 |
| NM_001098634 // RBM47 // RNA binding motif protein 47 // 4p14 // 54502 /// NM_01 | RBM47 | NM_001098634 | 0.00857247 | 2.30203 |
| NM_080658 // ACY3 // aspartoacylase (aminocyclase) 3 // 11q13.2 // 91703 /// ENS | ACY3 | NM_080658 | 0.0498753 | 2.301 |
| NR_003587 // MYO15B // myosin XVB pseudogene // 17q25.1 // 80022 /// BC027875 // | MYO15B | NR_003587 | 0.00759021 | 2.29754 |
| NM_005435 // ARHGEF5 // Rho guanine nucleotide exchange factor (GEF) 5 // 7q33-q | ARHGEF5 | NM_005435 | 0.00766916 | 2.29684 |
| NM_005435 // ARHGEF5 // Rho guanine nucleotide exchange factor (GEF) 5 // 7q33-q | ARHGEF5 | NM_005435 | 0.00846455 | 2.29311 |
| NM_001017967 // MARVELD3 // MARVEL domain containing 3 // 16q22.2 // 91862 /// N | MARVELD3 | NM_001017967 | 0.0124186 | 2.2921 |
| NM_003389 // CORO2A // coronin, actin binding protein, 2A // 9q22.3 // 7464 /// | CORO2A | NM_003389 | 0.0203606 | 2.28709 |
| NM_031469 // SH3BGRL2 // SH3 domain binding glutamic acid-rich protein like 2 // | SH3BGRL2 | NM_031469 | 0.0214373 | 2.27245 |
| NM_030766 // BCL2L14 // BCL2-like 14 (apoptosis facilitator) // 12p13-p12 // 793 | BCL2L14 | NM_030766 | 0.0037691 | 2.26634 |
| NR_002713 // NPY6R // neuropeptide Y receptor Y6 (pseudogene) // 5q31 // 4888 // | NPY6R | NR_002713 | 0.0429642 | 2.26407 |
| NM_001114086 // CLIC5 // chloride intracellular channel 5 // 6p12.3 // 53405 /// | CLIC5 | NM_001114086 | 0.0269601 | 2.25433 |
| NM_003645 // SLC27A2 // solute carrier family 27 (fatty acid transporter), membe | SLC27A2 | NM_003645 | 0.040906 | 2.2539 |
| NM_001136050 // DHRS1 // dehydrogenase/reductase (SDR family) member 1 // 14q12 | DHRS1 | NM_001136050 | 0.000608529 | 2.23931 |
| NM_002164 // IDO1 // indoleamine 2,3-dioxygenase 1 // 8p12-p11 // 3620 /// ENST0 | IDO1 | NM_002164 | 0.00532092 | 2.2314 |
| NM_001171192 // GDPD2 // glycerophosphodiester phosphodiesterase domain containi | GDPD2 | NM_001171192 | 0.0455387 | 2.23073 |
| NM_016445 // PLEK2 // pleckstrin 2 // 14q23.3 // 26499 // ENST00000216446 // PL | PLEK2 | NM_016445 | 0.0184048 | 2.22972 |
| NR_033122 // PDZD3 // PDZ domain containing 3 // 11q23.3 // 79849 /// NM_0011684 | PDZD3 | NR_033122 | 0.0104609 | 2.2269 |
| NM_000932 // PLCB3 // phospholipase C, beta 3 (phosphatidylinositol-specific) // | PLCB3 | NM_000932 | 0.01393 | 2.22018 |
| NM_018235 // CNDP2 // CNDP dipeptidase 2 (metallopeptidase M20 family) // 18q22. | CNDP2 | NM_018235 | 0.000958173 | 2.20566 |
| NM_032562 // PLA2G12B // phospholipase A2, group XIIB // 10q22.1 // 84647 /// EN | PLA2G12B | NM_032562 | 0.0420214 | 2.20423 |
| NM_021080 // DAB1 // disabled homolog 1 (Drosophila) // 1p32-p31 // 1600 /// ENS | DAB1 | NM_021080 | 0.04076 | 2.20106 |
| NM_001710 // CFB // complement factor B // 6p21.3 // 629 /// ENST00000425368 // | CFB | NM_001710 | 0.00181667 | 2.19954 |
| NM_183240 // TMEM37 // transmembrane protein 37 // 2q14.2 // 140738 /// ENST0000 | TMEM37 | NM_183240 | 0.0487149 | 2.19842 |
| AK127847 // FLJ45950 // FLJ45950 protein // 11q24.3 // 399975 | FLJ45950 | AK127847 | 0.00195329 | 2.198 |
| NM_001710 // CFB // complement factor B // 6p21.3 // 629 /// ENST00000417261 // | CFB | NM_001710 | 0.00220919 | 2.19758 |
| NM_144590 // ANKRD22 // ankyrin repeat domain 22 // 10q23.31 // 118932 /// ENST0 | ANKRD22 | NM_144590 | 0.0445105 | 2.19752 |
| NM_002067 // GNA11 // guanine nucleotide binding protein (G protein), alpha 11 ( | GNA11 | NM_002067 | 0.014093 | 2.19185 |
| NM_006579 // EBP // emopamil binding protein (sterol isomerase) // Xp11.23-p11.2 | EBP | NM_006579 | 0.0115147 | 2.18786 |
| NM_014873 // LPGAT1 // lysophosphatidylglycerol acyltransferase 1 // 1q32 // 992 | LPGAT1 | NM_014873 | 0.000550666 | 2.18469 |
| NM_030943 // AMN // amnionless homolog (mouse) // 14q32.3 // 81693 /// ENST00000 | AMN | NM_030943 | 0.00168811 | 2.18289 |
| NM_016548 // GOLM1 // golgi membrane protein 1 // 9q21.33 // 51280 // NM_177937 | GOLM1 | NM_016548 | 0.0424472 | 2.18243 |
| NM_032148 // SLC41A2 // solute carrier family 41, member 2 // 12q23.3 // 84102 / | SLC41A2 | NM_032148 | 0.0301277 | 2.17752 |

TABLE 2-continued

| Gene Information | Gene Symbol | RefSeq | p-value (CC vs UC) | Fold Increase |
|---|---|---|---|---|
| NM_000949 // PRLR // prolactin receptor // 5p13.2 // 5618 /// ENST00000382002 // | PRLR | NM_000949 | 0.0313649 | 2.17608 |
| NM_181642 // SPINT1 // serine peptidase inhibitor, Kunitz type 1 // 15q15.1 // 6 | SPINT1 | NM_181642 | 0.0361797 | 2.17498 |
| NM_001113567 // C17orf76 // chromosome 17 open reading frame 76 // 17p11.2 // 38 | C17orf76 | NM_001113567 | 0.0248369 | 2.17219 |
| NM_000355 // TCN2 // transcobalamin II // 22q12.2 // 6948 /// NM_001184726 // TC | TCN2 | NM_000355 | 0.0233279 | 2.17134 |
| NM_015198 // COBL // cordon-bleu homolog (mouse) // 7p12.1 / 23242 /// ENST0000 | COBL | NM_015198 | 0.0208672 | 2.1656 |
| NM_024616 // C3orf52 // chromosome 3 open reading frame 52 // 3q13.2 // 79669 // | C3orf52 | NM_024616 | 0.00881101 | 2.16302 |
| NM_020469 // ABO // ABO blood group (transferase A, alpha 1-3-N-acetylgalactosam | ABO | NM_020469 | 0.00222828 | 2.16292 |
| NM_030908 // OR2A4 // olfactory receptor, family 2, subfamily A, member 4 // 6q2 | OR2A4 | NM_030908 | 0.00568966 | 2.15894 |
| NM_003980 // MAP7 // microtubule-associated protein 7 // 6q23.3 // 9053 /// NM_0 | MAP7 | NM_003980 | 0.0037529 | 2.15742 |
| NM_017417 // GALNT8 // UDP-N-acetyl-alpha-D-galactosamine:polypeptide N-acetylga | GALNT8 | NM_017417 | 0.013696 | 2.15417 |
| NM_005410 // SEPP1 // selenoprotein P, plasma, 1 // 5q31 // 6414 /// NM_00108548 | SEPP1 | NM_005410 | 0.0133071 | 2.15347 |
| NM_152573 // RASEF // RAS and EF-hand domain containing // 9q21.32 // 158158 /// | RASER | NM_152573 | 0.0366785 | 2.15133 |
| NM_006633 // IQGAP2 // IQ motif containing GTPase activating protein 2 // 5q13.3 | IQGAP2 | NM_006633 | 0.00969849 | 2.1509 |
| NM_152550 // SH3RF2 // SH3 domain containing ring finger 2 // 5932 // 153769 /// | SH3RF2 | NM_152550 | 0.00614396 | 2.15072 |
| NM_018686 // CMAS // cytidine monophosphate N-acetylneuraminic acid synthetase / | CMAS | NM_018686 | 0.0124234 | 2.14998 |
| NM_025045 // BAIAP2L2 // BAI1-associated protein 2-like 2 // 22q13.1 // 80115 // | BAIAP2L2 | NM_025045 | 0.0129162 | 2.14195 |
| NM_001859 // SLC31A1 // solute carrier family 31 (copper transporters), member 1 | SLC31A1 | NM_001859 | 0.00838827 | 2.13821 |
| NM_016614 // TDP2 // tyrosyl-DNA phosphodiesterase 2 // 6p22.3-p22.1 // 51567 // | TDP2 | NM_016614 | 0.0246156 | 2.13573 |
| NM_003848 // SUCLG2 // succinate-CoA ligase, GDP-forming, beta subunit // 3p14.1 | SUCLG2 | NM_003848 | 0.00569037 | 2.13077 |
| NM_017904 // TTC22 // tetratricopeptide repeat domain 22 // 1p32.3 // 55001 //// | TTC22 | NM_017904 | 0.0153126 | 2.12827 |
| NM_003060 // SLC22A5 // solute carrier family 22 (organic cation/carnitine trans | SLC22A5 | NM_003060 | 0.02024 | 2.12394 |
| NM_002662 // PLD1 // phospholipase D1, phosphatidylcholine-specific // 3q26 // 5 | PLD1 | NM_002662 | 0.0135876 | 2.12113 |
| NM_018964 // SLC37A1 // solute carrier family 37 (glycerol-3-phosphate transport | SLC37A1 | NM_018964 | 0.0229039 | 2.12062 |
| NM_001251 // CD68 // CD68 molecule // 17p13 // 968 /// NM_001040059 // CD68 // C | CD68 | NM_001251 | 0.00105743 | 2.11575 |
| NM_174941 // CD163L1 // CD163 molecule-like 1 // 12p13.3 // 283316 /// ENST00000 | CD163L1 | NM_174941 | 0.00407203 | 2.11396 |
| NM_016029 // DHRS7 // dehydrogenase/reductase (SDR family) member 7 // 14q23.1 / | DHRS7 | NM_016029 | 0.0124063 | 2.11159 |
| NM_024101 // MLPH // melanophilin // 2q37.3 // 79083 /// NM_001042467 // MLPH // | MLPH | NM_024101 | 0.00197625 | 2.10533 |
| NM_004670 // PAPSS2 // 3'-phosphoadenosine 5'-phosphosulfate synthase 2 // 10q24 | PAPSS2 | NM_004670 | 0.0403309 | 2.10272 |
| AK172782 // GPAM // glycerol-3-phosphate acyltransferase, mitochondrial // 10q25 | GPAM | AK172782 | 0.0314353 | 2.09633 |
| NM_001142685 // ARHGAP32 // Rho GTPase activating protein 32 // 11q24.3 // 9743 | ARHGAP32 | NM_001142685 | 0.00415504 | 2.09203 |
| NM_198495 // CTAGE4 // CTAGE family, member 4 // 7q35 // 100128553 /// NM_001145 | CTAGE4 | NM_198495 | 0.00141321 | 2.0906 |
| ENST00000439698 // P4HA2 // prolyl 4-hydroxylase, alpha polypeptide II // 5q31 / | P4HA2 | ENST00000439698 | 0.0142839 | 2.08741 |
| NM_015020 // PHLPP2 // PH domain and leucine rich repeat protein phosphatase 2 / | PHLPP2 | NM_015020 | 0.013905 | 2.08634 |

TABLE 2-continued

| Gene Information | Gene Symbol | RefSeq | p-value (CC vs UC) | Fold Increase |
|---|---|---|---|---|
| NM_004252 // SLC9A3R1 // solute carrier family 9 (sodium/hydrogen exchanger), me | SLC9A3R1 | NM_004252 | 0.00776993 | 2.0857 |
| NM_012243 // SLC35A3 // solute carrier family 35 (UDP-N-acetylglucosamine (UDP-G | SLC35A3 | NM_012243 | 0.0307101 | 2.07986 |
| NM_020184 // CNNM4 // cyclin M4 // 2q11 // 26504 /// ENST00000377075 // CNNM4 // | CNNM4 | NM_020184 | 0.02685 | 2.07897 |
| NM_001490 // GCNT1 // glucosaminyl (N-acetyl) transferase 1, core 2 // 9q13 // 2 | GCNT1 | NM_001490 | 0.00172819 | 2.07671 |
| NM_003667 // LGR5 // leucine-rich repeat-containing G protein-coupled receptor 5 | LGR5 | NM_003667 | 0.0237574 | 2.07254 |
| NM_001966 // EHHADH // enoyl-CoA, hydratase/3-hydroxyacyl CoA dehydrogenase // 3 | EHHADH | NM_001966 | 0.0130422 | 2.07114 |
| NM_017726 // PPP1R14D // protein phosphatase 1, regulatory (inhibitor) subunit 1 | PPP1R14D | NM_017726 | 0.0497008 | 2.07017 |
| NM_006994 // BTN3A3 // butyrophilin, subfamily 3, member A3 // 6p21.3 // 10384 / | BTN3A3 | NM_006994 | 0.00121808 | 2.06925 |
| NM_001039724 // NOSTRIN // nitric oxide synthase trafficker // 2q31.1 // 115677 | NOSTRIN | NM_001039724 | 0.00986343 | 2.06731 |
| NR_026912 // ABHD11 // abhydrolase domain containing 11 // 7q11.23 // 83451 /// | ABHD11 | NR_026912 | 0.000593971 | 2.05896 |
| NM_001145206 // KIAA1671 // KIAA1671 // 22q11.23 // 85379 /// ENST00000358431 // | KIAA1671 | NM_001145206 | 0.00446756 | 2.05612 |
| NM_153345 // TMEM139 // transmembrane protein 139 // 7q34 // 135932 /// ENST0000 | TMEM139 | NM_153345 | 0.00505302 | 2.05293 |
| NM_001164694 // IYD // iodotyrosine deiodinase // 6q25.1 // 389434 /// NM_203395 | IYD | NM_001164694 | 0.022189 | 2.05208 |
| NM_016472 // C14orf129 // chromosome 14 open reading frame 129 // 14q32.2 // 515 | C14orf129 | NM_016472 | 0.048055 | 2.04519 |
| NM_001017402 // LAMB3 // laminin, beta 3 // 1q32 // 3914 /// NM_001127641 // LAM | LAMB3 | NM_001017402 | 0.0267716 | 2.04174 |
| NM_004999 // MYO6 // myosin VI // 6q13 // 4646 /// ENST00000369977 // MYO6 // my | MYO6 | NM_004999 | 0.00369349 | 2.04095 |
| NR_027244 // LOC151009 // hypothetical LOC151009 // 2q13 // 151009 /// NR 027244 | LOC151009 | NR_027244 | 0.0115721 | 2.04078 |
| AB065085 // TOM1L1 // target of myb1 (chicken)-like 1 // 17q23.2 // 10040 | TOM1L1 | AB065085 | 0.04656 | 2.03713 |
| NM_017750 // RETSAT // retinol saturase (all-trans-retinol 13,14-reductase) // 2 | RETSAT | NM_017750 | 0.0184264 | 2.03345 |
| NM_004721 // MAP3K13 // mitogen-activated protein kinase kinase kinase 13 // 3q2 | MAP3K13 | NM_004721 | 0.00937615 | 2.03148 |
| NM_018677 // ACSS2 // acyl-CoA synthetase short-chain family member 2 // 20q11.2 | ACSS2 | NM_018677 | 0.0306269 | 2.02661 |
| NM_014317 // PDSS1 // prenyl (decaprenyl) diphosphate synthase, subunit 1 // 10p | PDSS1 | NM_014317 | 0.0365076 | 2.02171 |
| NM_014498 // GOLIM4 // golgi integral membrane protein 4 // 3q26.2 // 27333 // | GOLIM4 | NM_014498 | 0.00240934 | 2.02056 |
| NM_033429 // CALML4 // calmodulin-like 4 // 15q23 // 91860 / NM_001031733 // C | CALML4 | NM_033429 | 0.0419784 | 2.01981 |
| NR_036751 // HSP90AA6P // heat shock protein 90kDa alpha (cytosolic), class A me | HSP90AA6P | NR_036751 | 0.0220954 | 2.01604 |
| NM_012120 // CD2AP // CD2-associated protein // 6p12 // 23607 /// ENST0000035931 | CD2AP | NM_012120 | 0.00502091 | 2.0122 |
| NM_005536 // IMPA1 // inositol(myo)-1(or 4)-monophosphatase 1 // 8q21.13-q21.3 / | IMPA1 | NM_005536 | 0.0194688 | 2.01203 |
| NM_001153 // ANXA4 // annexin A4 // 2p13 // 307 /// ENST00000394295 // ANXA4 // | ANXA4 | NM_001153 | 0.0255723 | 2.01151 |
| NM_000147 // FUCA1 // fucosidase, alpha-L- 1, tissue // 1p34 // 2517 /// ENST000 | FUCA1 | NM_000147 | 0.00469253 | 2.0105 |
| NM_003774 // GALNT4 // UDP-N-acetyl-alpha-D-galactosamine:polypeptide N-acetylga | GALNT4 | NM_003774 | 0.00622316 | 2.00871 |
| NM_001122890 // GGT6 // gamma-glutamyltransferase 6 // 17p13.2 // 124975 /// NM | GGT6 | NM_001122890 | 0.0328357 | 2.00627 |
| NM_001164277 // SLC37A4 // solute carrier family 37 (glucose-6-phosphate transpo | SLC37A4 | NM_001164277 | 0.0068184 | 2.00477 |

TABLE 2-continued

| Gene Information | Gene Symbol | RefSeq | p-value (CC vs UC) | Fold Increase |
|---|---|---|---|---|
| NM_001565 // CXCL 10 // chemokine (C-X-C motif) ligand 10 // 4q21 // 3627 /// ENS | CXCL10 | NM_001565 | 0.0468134 | 2.00368 |
| NM_005030 // PLK1 // polo-like kinase 1 // 16p12.2 // 5347 /// ENST00000300093 / | PLK1 | NM_005030 | 0.0109795 | 2.00251 |
| NM_001012631 // IL32 // interleukin 32 // 16p13.3 // 9235 /// NM_004221 // IL32 | IL32 | NM_001012631 | 0.0214868 | 2.00238 |
| NM_005309 // GPT // glutamic-pyruvate transaminase (alanine aminotransferase) // | GPT | NM_005309 | 0.0098254 | 2.00201 |
| NM_005159 // ACTC1 // actin, alpha, cardiac muscle 1 // 15q11-q14 // 70 /// ENST | ACTC1 | NM_005159 | 0.00451989 | −2.00712 |
| NM_130385 // MRVI1 // murine retrovirus integration site 1 homolog // 11p15 // 1 | MRVI1 | NM_130385 | 0.0186352 | −2.00908 |
| NR_003329 // SNORD116-14 // small nucleolar RNA, C/D box 116-14 // 15q11.2 // 10 | SNORD116-14 | NR_003329 | 0.00710694 | −2.01066 |
| NM_030751 // ZEB1 // zinc finger E-box binding homeobox 1 // 10p11.2 // 6935 /// | ZEB1 | NM_030751 | 0.0190641 | −2.01665 |
| NM_001321 // CSRP2 // cysteine and glycine-rich protein 2 // 12q21.1 // 1466 /// | CSRP2 | NM_001321 | 0.0130189 | −2.01975 |
| NM_199460 // CACNA1C // calcium channel, voltage-dependent, L type, alpha 1C sub | CACNA1C | NM_199460 | 0.0164629 | 2.03364 |
| NM_007078 // LDB3 // LIM domain binding 3 // 10q22.3-q23.2 // 11155 /// NM_00117 | LDB3 | NM_007078 | 0.013344 | −2.03636 |
| ENST00000436525 // C15orf51 // dynamin 1 pseudogene // 15q26.3 // 196968 | C15orf51 | ENST00000436525 | 0.0479813 | −2.04311 |
| ENST00000436525 // C15orf51 // dynamin 1 pseudogene // 15q26.3 // 196968 | C15orf51 | ENST00000436525 | 0.0479813 | −2.04311 |
| NM_001042454 // TGFB1I1 // transforming growth factor beta 1 induced transcript | TGFB1I1 | NM_001042454 | 0.0141045 | 2.0503 |
| NM_201266 // NRP2 // neuropilin 2 // 2q33.3 // 8828 /// NM_003872 // NRP2 // neu | NRP2 | NM_201266 | 0.0231808 | 2.05329 |
| NM_014286 // NCS1 // neuronal calcium sensor 1 // 9q34 // 23413 /// NM_001128826 | NCS1 | NM_014286 | 0.0400809 | −2.05571 |
| NR_002960 // SNORA20 // small nucleolar RNA, H/ACA box 20 // 6g25.3 // 677806 | SNORA20 | NR_002960 | 0.0102255 | −2.05618 |
| NR_023343 // RNU4ATAC // RNA, U4atac small nuclear (U12-dependent splicing) // 2 | RNU4ATAC | NR_023343 | 0.0114016 | −2.05953 |
| NM_003829 // MPDZ // multiple PDZ domain protein // 9p23 // 8777 /// ENST0000038 | MPDZ | NM_003829 | 0.0230169 | −2.06542 |
| NM_182734 // PLCB1 // phospholipase C, beta 1 (phosphoinositide-specific) // 20p | PLCB1 | NM_182734 | 0.0285626 | −2.0675 |
| NM_212482 // FN1 // fibronectin 1 // 2q34 // 2335 /// NM_002026 // FN1 // fibron | FN1 | NM_212482 | 0.0289963 | −2.06817 |
| NM_001166292 // PTCH2 // patched 2 // 1p34.1 // 8643 /// ENST00000438067 // PTCH | PTCH2 | NM_001166292 | 0.0155977 | −2.06949 |
| NM_001128310 // SPARCL1 // SPARC-like 1 (hevin) // 4q22.1 // 8404 /// NM_004684 | SPARCL1 | NM_001128310 | 0.0275433 | −2.0695 |
| NR_003332 // SNORD116-17 // small nucleolar RNA, C/D box 116-17 // 15q11.2 / 10 | SNORD116-17 | NR_003332 | 0.00123218 | −2.07085 |
| NR_003332 // SNORD116-17 // small nucleolar RNA, C/D box 116-17 // 15q11.2 / 10 | SNORD116-17 | NR_003332 | 0.00123218 | −2.07085 |
| NM_001390 // DTNA // dystrobrevin, alpha // 18q12 // 1837 /// NM_032975 // DTNA | DTNA | NM_001390 | 0.0140008 | −2.07227 |
| NM_172316 // MEIS2 // Meis homeobox 2 // 15q14 // 4212 /// NM_170677 // MEIS2 // | MEIS2 | NM_172316 | 0.012629 | −2.07482 |
| NM_032801 // JAM3 // junctional adhesion molecule 3 // 11q25 // 83700 /// ENST00 | JAM3 | NM_032801 | 0.00375191 | −2.08055 |
| NM_001496 // GFRA3 // GDNF family receptor alpha 3 // 5q31.1-q31.3 // 2676 // E | GFRA3 | NM_001496 | 0.0143176 | −2.08436 |
| NM_003116 // SPAG4 // sperm associated antigen 4 // 20q11.21 // 6676 /// ENST000 | SPAG4 | NM_003116 | 0.0370178 | −2.09743 |
| NR_002754 // RNU5E // RNA, U5E small nuclear // 1p36.22 // 26829 /// M77839 // R | RNU5E | NR_002754 | 0.0153145 | −2.10499 |
| NM_000109 // DMD // dystrophin // Xp21.2 // 1756 /// NM_004010 // DMD // dystrop | DMD | NM_000109 | 0.0305823 | −2.10535 |
| NM_005725 // TSPAN2 // tetraspanin 2 // 1p13.2 // 10100 /// ENST00000369516 // T | TSPAN2 | NM_005725 | 0.00484522 | −2.10726 |
| ENST00000436525 // C15orf51 // dynamin 1 pseudogene // 15q26.3 // 196968 | C15orf51 | ENST00000436525 | 0.0401346 | −2.11861 |
| NM_001190839 // MGP // matrix Gla protein // 12p12.3 // 4256 /// NM_000900 // MG | MGP | NM_001190839 | 0.0229696 | −2.13146 |

TABLE 2-continued

| Gene Information | Gene Symbol | RefSeq | p-value (CC vs UC) | Fold Increase |
|---|---|---|---|---|
| NM_031442 // TMEM47 // transmembrane protein 47 // Xp11.4 // 83604 /// ENST00000 | TMEM47 | NM_031442 | 0.0162367 | −2.16059 |
| NM_002776 // KLK10 // kallikrein-related peptidase 10 // 19q13 // 5655 /// NM_14 | KLK10 | NM_002776 | 0.0131782 | −2.16442 |
| NM_134269 // SMTN // smoothelin // 22q12.2 // 6525 /// NM_134270 // SMTN // smoo | SMTN | NM_134269 | 0.0278447 | −2.16615 |
| NM_002742 // PRKD1 // protein kinase D1 // 14q11 // 5587 /// ENST00000331968 // | PRKD1 | NM_002742 | 0.0208525 | −2.17797 |
| NM_001001396 // ATP2B4 // ATPase, Ca++ transporting, plasma membrane 4 // 1q32.1 | ATP2B4 | NM_001001396 | 0.0372252 | −2.18014 |
| NM_005451 // PDLIM7 // PDZ and LIM domain 7 (enigma) // 5q35.3 // 9260 /// NM_20 | PDLIM7 | NM_005451 | 0.00654348 | −2.18595 |
| NR_002952 // SNORA9 // small nucleolar RNA, H/ACA box 9 // 7p13 // 677798 /// AK | SNORA9 | NR_002952 | 0.0244704 | −2.19918 |
| NM_003069 // SMARCA1 // SWI/SNF related, matrix associated, actin dependent regu | SMARCA1 | NM_003069 | 0.00571381 | −2.2109 |
| NR_003330 // SNORD116-15 // small nucleolar RNA, C/D box 116-15 // 15q11.2 // 10 | SNORD116-15 | NR_003330 | 6.72E−05 | 2.21218 |
| NM_002398 // MEIS1 // Meis homeobox 1 // 2p14 // 4211 /// ENST00000272369 // MEI | MEIS1 | NM_002398 | 0.0208728 | −2.21341 |
| ENST00000436525 // C15orf51 // dynamin 1 pseudogene // 15q26.3 // 196968 | C15orf51 | ENST00000436525 | 0.0297132 | −2.22015 |
| ENST00000436525 // C15orf51 / dynamin 1 pseudogene // 15q26.3 // 196968 | C15orf51 | ENST00000436525 | 0.0297132 | −2.22015 |
| NM_003734 // AOC3 // amine oxidase, copper containing 3 (vascular adhesion prote | AOC3 | NM_003734 | 0.0151647 | −2.22019 |
| AF391113 // C21orf70 // chromosome 21 open reading frame 70 // 21q22.3 // 85395 | C21orf70 | AF391113 | 0.00109586 | −2.22308 |
| NM_001937 // DPT // dermatopontin // 1q12-q23 // 1805 /// ENST00000367817 // DPT | DPT | NM_001937 | 0.0379186 | −2.22359 |
| NM_012232 // PTRF // polymerase I and transcript release factor // 17q21.2 // 28 | PTRF | NM_012232 | 0.0194925 | −2.23107 |
| NM_024605 // ARHGAP10 // Rho GTPase activating protein 10 // 4q31.23 // 79658 // | ARHGAP10 | NM_024605 | 0.00832518 | −2.23204 |
| NM_022117 // TSPYL2 // TSPY-like 2 // Xp11.2 // 64061 /// ENST00000375442 // TSP | TSPYL2 | NM_022117 | 0.0134024 | −2.23502 |
| NM_005100 // AKAP12 // A kinase (PRKA) anchor protein 12 // 6q24-q25 // 9590 /// | AKAP12 | NM_005100 | 0.0357306 | 2.24089 |
| AY423733 // DDR2 // discoidin domain receptor tyrosine kinase 2 // 1q23.3 // 492 | DDR2 | AY423733 | 0.0358613 | −2.2447 |
| NM_153703 // PODN // podocan // 1p32.3 // 127435 /// ENST00000312553 // PODN // | PODN | NM_153703 | 0.0277365 | −2.26923 |
| NM_004370 // COL12A1 // collagen, type XII, alpha 1 // 6q12-q13 // 1303 // NM_0 | COL12A1 | NM_004370 | 0.0499701 | −2.27002 |
| NM_004137 // KCNMB1 // potassium large conductance calcium-activated channel, su | KCNMB1 | NM_004137 | 0.0277682 | −2.27584 |
| NM_014575 // SCHIP1 // schwannomin interacting protein 1 // 3q25.32-q25.33 // 29 | SCHIP1 | NM_014575 | 0.00470657 | −2.28272 |
| NM_001753 // CAV1 // caveolin 1, caveolae protein, 22kDa // 7q31.1 // 857 /// NM | CAV1 | NM_001753 | 0.0368534 | 2.29054 |
| NM_002338 // LSAMP // limbic system-associated membrane protein // 3q13.2-q21 // | LSAMP | NM_002338 | 0.0456749 | −2.30408 |
| NM_058229 // FBXO32 // F-box protein 32 // 8q24.13 // 114907 /// NM_148177 // FB | FBXO32 | NM_058229 | 0.0422526 | −2.30763 |
| NM_006765 // TUSC3 // tumor suppressor candidate 3 // 8p22 // 7991 /// NM_178234 | TUSC3 | NM_006765 | 0.00173576 | −2.32217 |
| NM_015687 // FILIP1 // filamin A interacting protein 1 // 6q14.1 // 27145 /// EN | FILIP1 | NM_015687 | 0.0158717 | −2.32321 |
| NM_006080 // SEMA3A // sema domain, immunoglobulin domain (Ig), short basic doma | SEMA3A | NM_006080 | 0.0142131 | −2.32699 |
| NM_000922 // PDE3B // phosphodiesterase 3B, cGMP-inhibited // 11p15.1 // 5140 // | PDE3B | NM_000922 | 0.00420057 | −2.33135 |
| NM_000722 // CACNA2D1 // calcium channel, voltage-dependent, alpha 2/delta subun | CACNA2D1 | NM_000722 | 0.0107345 | −2.33411 |
| NM_001197294 // DPYSL3 // dihydropyrimidinase-like 3 // 5q32 // 1809 /// NM_0013 | DPYSL3 | NM_001197294 | 0.0231385 | −2.33517 |

TABLE 2-continued

| Gene Information | Gene Symbol | RefSeq | p-value (CC vs UC) | Fold Increase |
|---|---|---|---|---|
| NM_172311 // STON1-GTF2A1L // STON1-GTF2A1L readthrough // 2p16.3 // 286749 /// | TON1-GTF2A1 | NM_172311 | 0.0264382 | −2.33729 |
| NM_000857 // GUCY1B3 // guanylate cyclase 1, soluble, beta 3 // 4q31.3-q33 // 29 | GUCY1B3 | NM_000857 | 0.0141507 | −2.34285 |
| NR_033662 // CSF3 // colony stimulating factor 3 (granulocyte) // 17q11.2-q12 // | CSF3 | NR_033662 | 0.036854 | −2.35397 |
| NM_001706 // BCL6 // B-cell CLL/lymphoma 6 // 3q27 // 604 /// NM_001130845 // BC | BCL6 | NM_001706 | 0.0395014 | −2.37213 |
| NM_014112 // TRPS1 // trichorhinophalangeal syndrome I // 8q24.12 // 7227 /// EN | TRPS1 | NM_014112 | 0.021813 | −2.37338 |
| NM_003275 // TMOD1 // tropomodulin 1 // 9q22.3 // 7111 /// NM_001166116 // TMOD1 | TMOD1 | NM_003275 | 0.00926909 | −2.39163 |
| NM_004040 // RHOB // ras homolog gene family, member B // 2p24 // 388 //// ENST00 | RHOB | NM_004040 | 0.00209611 | −2.39166 |
| NM_007281 // SCRG1 // stimulator of chondrogenesis 1 // 4q34.1 // 11341 /// ENST | SCRG1 | NM_007281 | 0.0449505 | −2.42771 |
| NM_053025 // MYLK // myosin light chain kinase // 3q21 // 4638 /// NM_053026 // | MYLK | NM_053025 | 0.0334323 | −2.44896 |
| NM_133646 // ZAK // sterile alpha motif and leucine zipper containing kinase AZK | ZAK | NM_133646 | 0.0101002 | −2.45225 |
| NM_001123364 // C6orf186 // chromosome 6 open reading frame 186 // 6q21 // 72846 | C6orf186 | NM_001123364 | 0.0338175 | −2.45305 |
| NM_005909 // MAP1B // microtubule-associated protein 1B // 5q13 // 4131 /// ENST | MAP1B | NM_005909 | 0.00199713 | −2.45363 |
| NM_001136191 // KANK2 // KN motif and ankyrin repeat domains 2 // 19p13.2 // 259 | KANK2 | NM_001136191 | 0.00418 | −2.45823 |
| NR_002836 // PGM5P2 // phosphoglucomutase 5 pseudogene 2 // 9q12 // 595135 // N | PGM5P2 | NR_002836 | 0.0106051 | −2.46207 |
| NM_006988 // ADAMTS1 // ADAM metallopeptidase with thrombospondin type 1 motif, | ADAMTS1 | NM_006988 | 0.0212926 | −2.47602 |
| NM_001897 // CSPG4 // chondroitin sulfate proteoglycan 4 // 15q24.2 // 1464 /// | CSPG4 | NM_001897 | 0.000233664 | −2.47738 |
| NM_012134 // LMOD1 // leiomodin 1 (smooth muscle) // 1q32 // 25802 /// ENST00000 | LMOD1 | NM_012134 | 0.0254164 | −2.48821 |
| NM_000856 // GUCY1A3 // guanylate cyclase 1, soluble, alpha 3 // 4q31.3-q33|4q31 | GUCY1A3 | NM_000856 | 0.0154068 | −2.49669 |
| NR_002196 // H19 // H19, imprinted maternally expressed transcript (non-protein | H19 | NR_002196 | 0.0422207 | −2.49895 |
| NM_002667 // PLN // phospholamban // 6q22.1 // 5350 /// ENST00000357525 // PLN / | PLN | NM_002667 | 0.0458219 | −2.50528 |
| NM_004078 // CSRP1 // cysteine and glycine-rich protein 1 // 1q32 // 1465 /// NM | CSRP1 | NM_004078 | 0.0389579 | −2.51599 |
| NM_001141945 // ACTA2 // actin, alpha 2, smooth muscle, aorta // 10q23.3 // 59 / | ACTA2 | NM_001141945 | 0.00367966 | −2.51621 |
| NM_002986 // CCL11 // chemokine (C-C motif) ligand 11 // 17q21.1-q21.2 // 6356 / | CCL11 | NM_002986 | 0.0132628 | −2.5178 |
| NM_033138 // CALD1 // caldesmon 1 // 7q33 // 800 /// NM_033157 // CALD1 // calde | CALD1 | NM_033138 | 0.0229067 | −2.51869 |
| NM_001164836 // FXYD6 // FXYD domain containing ion transport regulator 6 // 11q | FXYD6 | NM_001164836 | 0.0202065 | −2.53004 |
| NM_003725 // HSD17B6 // hydroxysteroid (17-beta) dehydrogenase 6 homolog (mouse) | HSD17B6 | NM_003725 | 0.0196889 | −2.54527 |
| NM_001146312 // MYOCD // myocardin // 17p11.2 // 93649 /// NM_153604 // MYOCD // | MYOCD | NM_001146312 | 0.0298805 | −2.59465 |
| NM_015225 // PRUNE2 // prune homolog 2 (Drosophila) // 9q21.2 // 158471 /// AB53 | PRUNE2 | NM_015225 | 0.0217217 | −2.59492 |
| NM_001168278 // WWTR1 // WW domain containing transcription regulator 1 // 3q23- | WWTR1 | NM_001168278 | 0.014475 | −2.60243 |
| NM_001008711 // RBPMS // RNA binding protein with multiple splicing // 8p12 // 1 | RBPMS | NM_001008711 | 0.00600769 | −2.60406 |
| NM_001014796 // DDR2 // discoidin domain receptor tyrosine kinase 2 // 1q23.3 // | DDR2 | NM_001014796 | 0.00523497 | −2.61121 |
| NM_018640 // LMO3 // LIM domain only 3 (rhombotin-like 2) // 12p12.3 // 55885 // | LMO3 | NM_018640 | 0.042971 | −2.63105 |
| NR_002836 // PGM5P2 // phosphoglucomutase 5 pseudogene 2 // 9q12 // 595135 // N | PGM5P2 | NR_002836 | 0.00678244 | −2.64929 |

TABLE 2-continued

| Gene Information | Gene Symbol | RefSeq | p-value (CC vs UC) | Fold Increase |
|---|---|---|---|---|
| NM_021914 // CFL2 // cofilin 2 (muscle) // 14q12 // 1073 /// NM_138638 // CFL2 / | CFL2 | NM_021914 | 0.0261349 | −2.65343 |
| NM_016277 // RAB23 // RAB23, member RAS oncogene family // 6p11 // 51715 // NM_ | RAB23 | NM_016277 | 0.035448 | −2.66122 |
| NM_145234 // CHRDL1 // chordin-like 1 // Xq23 // 91851 /// NM_001143981 // CHRDL | CHRDL1 | NM_145234 | 0.00265317 | −2.67563 |
| NM_001134439 // PHLDB2 // pleckstrin homology-like domain, family B, member 2 // | PHLDB2 | NM_001134439 | 0.0258326 | −2.67775 |
| NM_006832 // FERMT2 // fermitin family member 2 // 14q22.1 // 10979 /// NM_00113 | FERMT2 | NM_006832 | 0.0205617 | −2.7145 |
| NM_001128205 // SULF1 // sulfatase 1 // 8q13.1 // 23213 /// NM_015170 // SULF1 / | SULF1 | NM_001128205 | 0.0335496 | −2.73234 |
| NM_194272 // RBPMS2 // RNA binding protein with multiple splicing 2 // 15q22.31 | RBPMS2 | NM_194272 | 0.012053 | 2.74286 |
| NM_014476 // PDLIM3 // PDZ and LIM domain 3 // 4q35 // 27295 /// NM_001114107 // | PDLIM3 | NM_014476 | 0.0110612 | −2.7574 |
| NM_015886 // PI15 // peptidase inhibitor 15 // 8q21.11 // 51050 /// ENST00000260 | PI15 | NM_015886 | 0.0312943 | −2.78937 |
| NM_003289 // TPM2 // tropomyosin 2 (beta) // 9p13 // 7169 /// NM_213674 // TPM2 | TPM2 | NM_003289 | 0.0272347 | −2.80338 |
| NM_001458 // FLNC // filamin C, gamma // 7q32-q35 // 2318 /// NM_001127487 // FL | FLNC | NM_001458 | 0.0113027 | −2.80588 |
| NM_006097 // MYL9 // myosin, light chain 9, regulatory // 20q11.23 // 10398 /// | MYL9 | NM_006097 | 0.0412118 | −2.81849 |
| NM_199460 // CACNA1C // calcium channel, voltage-dependent, L type, alpha 1C sub | CACNA1C | NM_199460 | 0.00694625 | −2.83404 |
| NM_001232 // CASQ2 // calsequestrin 2 (cardiac muscle) // 1p13.3-p11 // 845 /// | CASQ2 | NM_001232 | 0.0349505 | −2.84886 |
| NM_001193460 // MSRB3 // methionine sulfoxide reductase B3 // 12q14.3 // 253827 | MSRB3 | NM_001193460 | 0.0108076 | −2.84899 |
| NM_001456 // FLNA // filamin A, alpha // Xq28 // 2316 /// NM_001110556 // FLNA / | FLNA | NM_001456 | 0.0164878 | −2.86026 |
| NM_006366 // CAP2 // CAP, adenylate cyclase-associated protein, 2 (yeast) // 6p2 | CAP2 | NM_006366 | 0.00596997 | −2.89059 |
| NM_001031701 // NT5DC3 // 5'-nucleotidase domain containing 3 // 12q22-q23.1 | NT5DC3 | NM_001031701 | 0.0464686 | −2.90347 |
| NM_003999 // OSMR // oncostatin M receptor // 5p13.1 // 9180 /// NM_001168355 | OSMR | NM_003999 | 0.0324297 | −2.92605 |
| NM_001885 // CRYAB // crystallin, alpha B // 11q22.3-q23.1 // 1410 /// ENST00000 | CRYAB | NM_001885 | 0.0163674 | −2.96044 |
| NM_000517 // HBA2 // hemoglobin, alpha 2 // 16p13.3 // 3040 /// BC101846 // HBA1 | HBA2 | NM_000517 | 0.0195505 | −3.10109 |
| NM_000558 // HBA1 // hemoglobin, alpha 1 // 16p13.3 // 3039 /// BC101846 // HBA1 | HBA1 | NM_000558 | 0.0195505 | −3.10109 |
| NM_004282 // BAG2 // BCL2-associated athanogene 2 // 6p12.1-p11.2 // 9532 /// EN | BAG2 | NM_004282 | 0.0108668 | −3.11097 |
| NM_022135 // POPDC2 // popeye domain containing 2 // 3q13.33 // 64091 /// ENST00 | POPDC2 | NM_022135 | 0.0219995 | −3.1427 |
| NM_001001522 // TAGLN // transgelin // 11q23.2 // 6876 /// NM_003186 // TAGLN // | TAGLN | NM_001001522 | 0.0148609 | −3.35842 |
| NM_212482 // FN1 // fibronectin 1 // 2q34 // 2335 /// NM_002026 // FN1 // fibron | FN1 | NM_212482 | 0.00987492 | −3.43741 |
| NM_133477 // SYNPO2 // synaptopodin 2 // 4q26 // 171024 /// NM_001128933 // SYNP | SYNPO2 | NM_133477 | 0.0241716 | −3.56252 |
| NM_000450 // SELE // selectin E // 1q22-q25 // 6401 /// ENST00000333360 // SELE | SELE | NM_000450 | 0.0460446 | −3.56423 |
| NR_029686 // MIR145 // microRNA 145 // 5q32 // 406937 /// NR_027180 // LOC728264 | MIR145 | NR_029686 | 0.0119026 | −3.58867 |
| NM_022648 // TNS1 // tensin 1 // 2q35-q36 // 7145 /// ENST00000171887 // TNS1 // | TNS1 | NM_022648 | 0.00555851 | −3.61273 |
| NM_001615 // ACTG2 // actin, gamma 2, smooth muscle, enteric // 2p13.1 // 72 /// | ACTG2 | NM_001615 | 0.0379131 | −3.62826 |
| NM_022844 // MYH11 // myosin, heavy chain 11, smooth muscle // 16p13.11 // 4629 | MYH11 | NM_022844 | 0.0240032 | −3.66415 |
| NM_002205 // ITGA5 // integrin, alpha 5 (fibronectin receptor, alpha polypeptide | ITGA5 | NM_002205 | 0.0207749 | −3.82521 |
| NM_001299 // CNN1 // calponin 1, basic, smooth muscle // 19p13.2-p13.1 // 1264 / | CNN1 | NM_001299 | 0.0413103 | −3.84711 |
| NM_001034954 // SORBS1 // sorbin and SH3 domain containing 1 // 10q23.33 // 1058 | SORBS1 | NM_001034954 | 0.00399907 | −3.89048 |

TABLE 2-continued

| Gene Information | Gene Symbol | RefSeq | p-value (CC vs UC) | Fold Increase |
|---|---|---|---|---|
| NM_001927 // DES // desmin // 2q35 // 1674 /// ENST00000373960 // DES // desmin | DES | NM_001927 | 0.0268126 | −3.90558 |
| NM_144617 // HSPB6 // heat shock protein, alpha-crystallin-related, B6 // 19q13. | HSPB6 | NM_144617 | 0.0145209 | −3.90993 |
| NM_015424 // CHRDL2 // chordin-like 2 // 11q14 // 25884 /// ENST00000263671 // C | CHRDL2 | NM_015424 | 0.0247555 | −4.23746 |
| NM_000518 // HBB // hemoglobin, beta // 11p15.5 // 3043 /// ENST00000335295 // H | HBB | NM_000518 | 0.0255665 | −4.3277 |
| NM_002160 // TNC // tenascin C // 9q33 // 3371 /// ENST00000350763 // TNC // ten | TNC | NM_002160 | 0.0126641 | −4.4403 |
| NM_006198 // PCP4 // Purkinje cell protein 4 // 21q22.2 // 5121 /// ENST00000328 | PCP4 | NM_006198 | 0.0340302 | −4.51736 |

TABLE 3

| Gene | LSMean (CC) | LSMean (UC) | p-value (CC vs. UC) | Ratio (CC vs. UC) | Fold-Change (CC vs. UC) |
|---|---|---|---|---|---|
| ALOX5AP | 6.5368 | 7.2279 | 0.153036 | 0.61938 | −1.61452 |
| CD53 | 8.15458 | 8.56075 | 0.417119 | 0.754626 | −1.32516 |
| CLEC4D | 3.24889 | 4.27055 | 0.168864 | 0.49255 | −2.03025 |
| CYP4F3LP | 4.37787 | 5.62699 | 0.0584598 | 0.420703 | −2.37697 |
| DEFA5 | 12.7353 | 5.85087 | 0.00182520 | 118.145 | 118.145 |
| IL6 | 4.49499 | 6.78934 | 0.167391 | 0.203859 | −4.90534 |
| RBP2 | 5.30406 | 2.51937 | 0.282548 | 6.8909 | 6.8909 |
| SAA1 | 8.41257 | 9.68772 | 0.0988763 | 0.413184 | −2.42023 |
| SAA2 | 5.51497 | 5.96818 | 0.575901 | 0.730416 | −1.36908 |
| SCARNA8 | 11.4046 | 12.1182 | 0.132287 | 0.609768 | −1.63997 |
| SMAD4 | 8.62326 | 9.2041 | 0.00233383 | 0.668575 | −1.49572 |
| SNORD13 | 17.8866 | 18.7927 | 0.00409278 | 0.533634 | −1.87394 |
| SNORD13P | 7.23404 | 7.74883 | 0.0839705 | 0.699895 | −1.42879 |
| SNORD28 | 15.5932 | 16.2543 | 0.00995582 | 0.632425 | −1.58122 |
| STAP1 | 5.59895 | 6.62415 | 0.211401 | 0.491342 | −2.03524 |
| UNQ2550 | 2.97077 | 3.95127 | 0.0386757 | 0.506805 | −1.97314 |

What is claimed is:

1. A method of diagnosing and treating inflammatory bowel disease (IBD) in a patient in need thereof, said method comprising:
   obtaining a sample from the patient;
   measuring an expression of DEFA5;
   comparing the expression of DEFA5 in the sample to a benchmark value that is typical of a subject not suffering from Crohn's disease; and
   either:
      diagnosing Crohn's disease if the expression of DEFA5 in the sample exceeds the benchmark value, and performing a non-surgical intervention on the patient to treat Crohn's disease; or
      diagnosing ulcerative colitis if the expression of DEFA5 in the sample does not exceed the benchmark value; and performing a surgical intervention on the patient to treat ulcerative colitis.

2. The method of claim 1, wherein the DEFA5 is human DEFA5.

3. The method of claim 1, wherein the sample is a blood sample, a serum sample, a stool sample, or an intestinal tissue sample.

4. The method of claim 1, wherein the patient displays one or more of severe diarrhea, abdominal pain, fatigue, and weight loss.

5. The method of claim 1, wherein the surgical intervention is selected from a proctocolectomy or an ileal pouch anal anastomosis.

6. The method of claim 1, wherein the non-surgical intervention is administration of a drug selected from the group consisting of: an iron supplement, an anti-inflammatory, a corticosteroid, hydrocortisone, cortisone, prednisolone, a 5-aminosalicylate, an immunosuppressant, azathioprine, mercaptopurine, cyclosporine, an anti-TNF-alpha antibody, infliximab, adalimumab, golimumab, methotrexate, an anti-α4-integrin antibody, vedolizumab, an antibacterial antibiotic, ciprofloxacin, metronidazole, suppository mesalazine, enema mesalazine, olsalazine, balsalazide, enema budesonide, tacrolimus, and a combination of any of the foregoing.

7. The method of claim 6, wherein the non-surgical intervention is administration of a drug selected from the group consisting of: cyclosporine, golimumab, and a combination thereof.

8. The method of claim 1, wherein the step of diagnosing ulcerative colitis further comprises diagnosing ulcerative colitis if the expression of DEFA5 in the sample is at a level of less than about $3 \times 10^6$ DEFA5 mRNA Transcript per 10 ng RNA.

9. The method of claim 1, wherein the step of diagnosing Crohn's disease further comprises diagnosing Crohn's disease if the expression of DEFA5 in the sample is at a level from about $3 \times 10^6$ to $1.2 \times 10^8$ DEFA5 mRNA Transcript per 10 ng RNA.

* * * * *

SEQUENCE LISTING

<160> NUMBER OF SEQ ID NOS: 6

<210> SEQ ID NO 1
<211> LENGTH: 94
<212> TYPE: PRT
<213> ORGANISM: Homo sapiens

<400> SEQUENCE: 1

Met Arg Thr Ile Ala Ile Leu Ala Ala Ile Leu Leu Val Ala Leu Gln
1               5                   10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
                85                  90

<210> SEQ ID NO 2
<211> LENGTH: 94
<212> TYPE: PRT
<213> ORGANISM: Homo sapiens

```
<400> SEQUENCE: 2

Met Arg Thr Leu Ala Ile Leu Ala Ala Ile Leu Leu Val Ala Leu Gln
 1               5                  10                  15

Ala Gln Ala Glu Pro Leu Gln Ala Arg Ala Asp Glu Val Ala Ala Ala
                20                  25                  30

Pro Glu Gln Ile Ala Ala Asp Ile Pro Glu Val Val Val Ser Leu Ala
            35                  40                  45

Trp Asp Glu Ser Leu Ala Pro Lys His Pro Gly Ser Arg Lys Asn Met
 50                  55                  60

Ala Cys Tyr Cys Arg Ile Pro Ala Cys Ile Ala Gly Glu Arg Arg Tyr
 65                  70                  75                  80

Gly Thr Cys Ile Tyr Gln Gly Arg Leu Trp Ala Phe Cys Cys
                85                  90

<210> SEQ ID NO 3
<211> LENGTH: 94
<212> TYPE: PRT
<213> ORGANISM: Homo Sapiens

<400> SEQUENCE: 3

Met Arg Thr Leu Ala Ile Leu Ala Ala Ile Leu Leu Val Ala Leu Gln
 1               5                  10                  15

Ala Gln Ala Glu Pro Leu Gln Ala Arg Ala Asp Glu Val Ala Ala Ala
                20                  25                  30

Pro Glu Gln Ile Ala Ala Asp Ile Pro Glu Val Val Val Ser Leu Ala
            35                  40                  45

Trp Asp Glu Ser Leu Ala Pro Lys His Pro Gly Ser Arg Lys Asn Met
 50                  55                  60

Ala Cys Tyr Cys Arg Ile Pro Ala Cys Ile Ala Gly Glu Arg Arg Tyr
 65                  70                  75                  80

Gly Thr Cys Ile Tyr Gln Gly Arg Leu Trp Ala Phe Cys Cys
                85                  90

<210> SEQ ID NO 4
<211> LENGTH: 94
<212> TYPE: PRT
<213> ORGANISM: Homo sapiens

<400> SEQUENCE: 4

Met Arg Thr Leu Ala Ile Leu Ala Ala Ile Leu Leu Val Ala Leu Gln
 1               5                  10                  15

Ala Gln Ala Glu Pro Leu Gln Ala Arg Ala Asp Glu Val Ala Ala Ala
                20                  25                  30

Pro Glu Gln Ile Ala Ala Asp Ile Pro Glu Val Val Val Ser Leu Ala
            35                  40                  45

Trp Asp Glu Ser Leu Ala Pro Lys His Pro Gly Ser Arg Lys Asn Met
 50                  55                  60

Asp Cys Tyr Cys Arg Ile Pro Ala Cys Ile Ala Gly Glu Arg Arg Tyr
 65                  70                  75                  80

Gly Thr Cys Ile Tyr Gln Gly Arg Leu Trp Ala Phe Cys Cys
                85                  90

<210> SEQ ID NO 5
<211> LENGTH: 97
<212> TYPE: PRT
<213> ORGANISM: Homo sapiens

<400> SEQUENCE: 5
```

```
Met Arg Ile Ile Ala Leu Leu Ala Ala Ile Leu Leu Val Ala Leu Gln
1               5                   10                  15

Val Arg Ala Gly Pro Leu Gln Ala Arg Gly Asp Glu Ala Pro Gly Gln
            20                  25                  30

Glu Gln Arg Gly Pro Glu Asp Gln Asp Ile Ser Ile Ser Phe Ala Trp
        35                  40                  45

Asp Lys Ser Ser Ala Leu Gln Val Ser Gly Ser Thr Arg Gly Met Val
    50                  55                  60

Cys Ser Cys Arg Leu Val Phe Cys Arg Arg Thr Glu Leu Arg Val Gly
65              70                  75                  80

Asn Cys Leu Ile Gly Gly Val Ser Phe Thr Tyr Cys Cys Thr Arg Val
                85                  90                  95

Asp

<210> SEQ ID NO 6
<211> LENGTH: 99
<212> TYPE: PRT
<213> ORGANISM: Homo sapiens

<400> SEQUENCE: 6

Met Arg Thr Leu Thr Ile Leu Thr Ala Val Leu Leu Val Ala Leu Gln
1               5                   10                  15

Ala Lys Ala Glu Pro Leu Gln Ala Glu Asp Asp Pro Leu Gln Ala Lys
            20                  25                  30

Ala Tyr Glu Ala Asp Ala Gln Glu Gln Arg Gly Ala Asn Asp Gln Asp
        35                  40                  45

Phe Ala Val Ser Phe Ala Glu Asp Ala Ser Ser Ser Leu Arg Ala Leu
    50                  55                  60

Gly Ser Thr Arg Ala Phe Thr Cys His Cys Arg Arg Ser Cys Tyr Ser
65              70                  75                  80

Thr Glu Tyr Ser Tyr Gly Thr Cys Thr Val Met Gly Ile Asn His Arg
                85                  90                  95

Phe Cys Cys
```